US011202850B2

(12) United States Patent
Bowlin et al.

(10) Patent No.: US 11,202,850 B2
(45) Date of Patent: Dec. 21, 2021

(54) COMPOSITIONS AND METHODS FOR INHIBITING INFLAMMATION

(71) Applicants: THE UNIVERSITY OF MEMPHIS RESEARCH FOUNDATION, Memphis, TN (US); THE UNIVERSITY OF TENNESSEE RESEARCH FOUNDATION, Memphis, TN (US)

(72) Inventors: Gary L. Bowlin, Memphis, TN (US); Allison E. Fetz, Memphis, TN (US); Marko Z. Radic, Memphis, TN (US)

(73) Assignees: The University of Memphis Research Foundation, Memphis, TN (US); The University of Tennessee Research Foundation, Memphis, TN (US)

( * ) Notice: Subject to any disclaimer, the term of this patent is extended or adjusted under 35 U.S.C. 154(b) by 0 days.

(21) Appl. No.: 16/298,891

(22) Filed: Mar. 11, 2019

(65) Prior Publication Data

US 2019/0275200 A1 Sep. 12, 2019

Related U.S. Application Data

(60) Provisional application No. 62/641,146, filed on Mar. 9, 2018.

(51) Int. Cl.

| | |
|---|---|
| ***A61L 27/18*** | (2006.01) |
| ***A61L 27/54*** | (2006.01) |
| ***A61L 27/58*** | (2006.01) |
| ***A61L 27/56*** | (2006.01) |
| ***A61P 29/00*** | (2006.01) |
| ***C08L 67/04*** | (2006.01) |
| ***C08G 63/06*** | (2006.01) |
| ***D01F 6/62*** | (2006.01) |
| ***D01D 5/00*** | (2006.01) |
| ***D01F 1/10*** | (2006.01) |
| ***C08K 5/29*** | (2006.01) |

(52) U.S. Cl.

CPC ............... *A61L 27/18* (2013.01); *A61L 27/54* (2013.01); *A61L 27/58* (2013.01); *A61P 29/00* (2018.01); *C08G 63/06* (2013.01); *D01D 5/0007* (2013.01); *D01F 1/10* (2013.01); *A61L 2300/204* (2013.01); *A61L 2300/41* (2013.01); *A61L 2300/434* (2013.01); *C08K 5/29* (2013.01); *C08L 67/04* (2013.01); *D01F 6/625* (2013.01)

(58) Field of Classification Search

None

See application file for complete search history.

(56) References Cited

U.S. PATENT DOCUMENTS

| | | | |
|---|---|---|---|
| 7,374,774 | B2 | 5/2008 | Bowlin et al. |
| 7,998,498 | B2 | 8/2011 | Szycher |
| 8,173,151 | B2 | 5/2012 | Szycher |
| 8,367,094 | B2 | 2/2013 | Szycher |

FOREIGN PATENT DOCUMENTS

WO 2016/118476 A1 7/2016

OTHER PUBLICATIONS

Sell et al ("Electrospun polydioxanone-elastin blends: potential for bioresorbable vascular grafts", Biomedical Materials, vol. 1(2), p. 72-80 (2006)) (Year: 2006).*

Gupta et al., "The Role of Neutrophils and NETosis in Autoimmune and Renal Diseases," Nat Rev Nephrol. 2016, vol. 12(7), pp. 403-413.

Kusunoki et al., "Peptidylarginine Deiminase Inhibitor Suppresses Neutrophil Extracellular trap Formation and MPO-ANCA Production," Frontiers in Immunology, 2016, vol. 7, pp. 1-7.

International Search Report and Written Opinion dated Jun. 3, 2019 in corresponding international application No. PCT/US19/21663 (10 pages).

Fetz et al.."Electrospun Template Architecture and Composition Regulate Neutrophil NETosis In Vitro and In Vivo," Tissue Engineering Part A, vol. 23, No. 19-20, Oct. 1, 2017, https://doi.org/10.1089/ten.tea.2016.0452.

Luo et al., "Inhibitors and Inactivators of Protein Arginine Deiminase 4: Functional and Structural Characterization," Biochemistry. 2006; 45(39):11727-11736.

Luo et al., "Activity Based Protein Profiling Reagents for Protein Arginine Deiminase 4 (PAD4): Synthesis and in vitro Evaluation of a Fluorescently-labeled Probe," J. Am. Chem Soc. 2006; 128(45): 14468-14469.

Kimmel, "Identification and Characterization of Specific Clones: Strategy for Confirming the Validity of Presumptive Clones," Methods in Enzymology, vol. 152, 1987, pp. 507-511.

Li et al. "Electrospun Protein Fibers as Matrices for Tissue Engineering," Biomaterials. Oct. 2005; 26(30):5999-6008.

Wahl et al., "Molecular Hybridization of Immobilized Nucleic Acids: Theoretical Concepts and Practical Considerations," Methods in Enzymology, vol. 152, 1987, pp. 399-407.

Extended European Search Report dated Oct. 12, 2021 in corresponding European Patent Application No. 19763242.5 (6 pages).

* cited by examiner

*Primary Examiner* — Sin J Lee

(74) *Attorney, Agent, or Firm* — Melissa Hunter-Ensor; Greenberg Traurig, LLP

(57) ABSTRACT

As described below, the present invention features compositions and methods for inhibiting inflammation in connection with an acellular template (e.g., an electrospun template). In one embodiment, the template is impregnated with an agent (e.g., N-α-benzoyl-N5-(2-chloro-1-iminoethyl)-L-ornithine amide (Cl-amidine)) that inhibits a peptidylarginine deaminase (e.g., PAD4).

12 Claims, 34 Drawing Sheets

Plot of drug concentration against relative fluorescence for HBSS and HFP exposed samples. Veh. is HBSS only. * indicates a significant difference in relative fluorescence ($p < 0.05$) (mean ± std. dev., $n = 4$)

3 Hours

6 Hours

3 Hours

Merge

Equation 2:
$$y = 91.1x$$
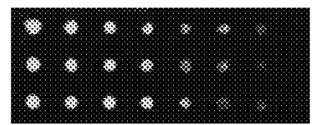
FIG. 15
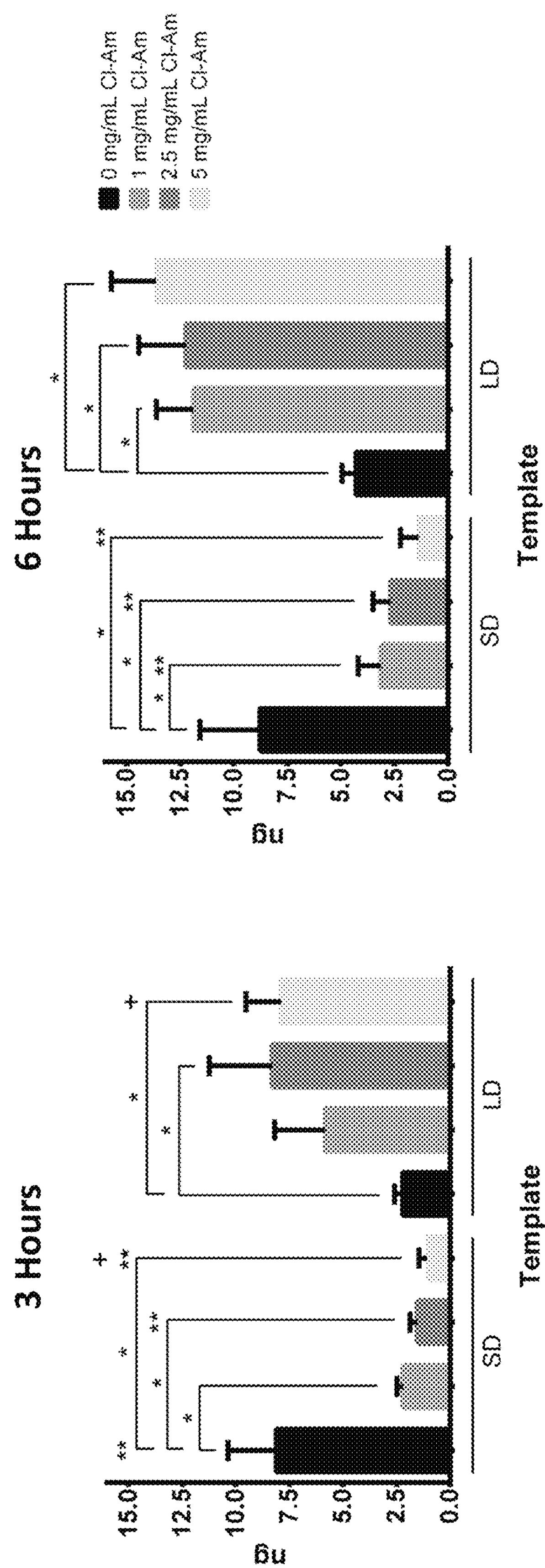
FIG. 16A
FIG. 16B

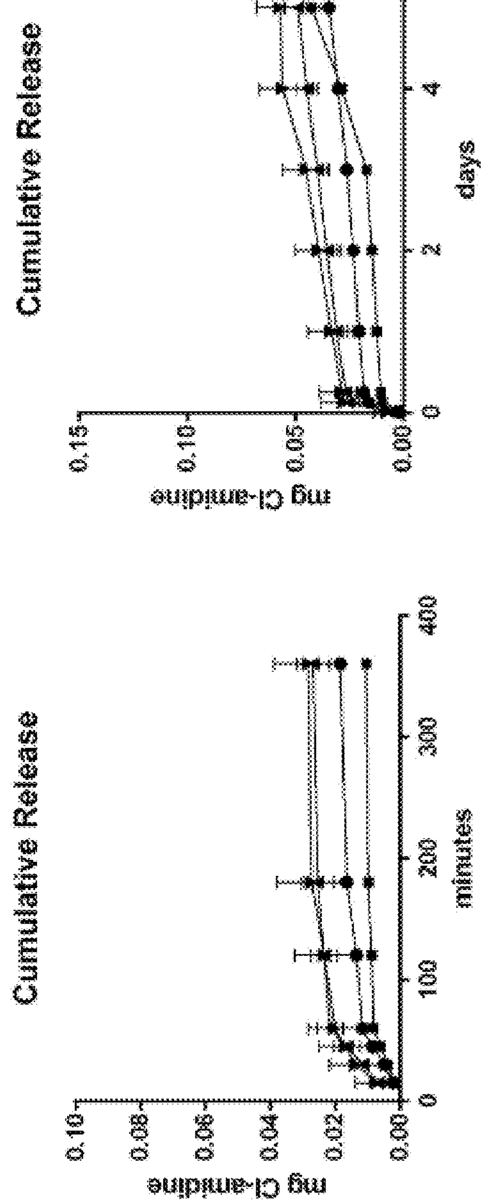
FIG. 21B
FIG. 21A
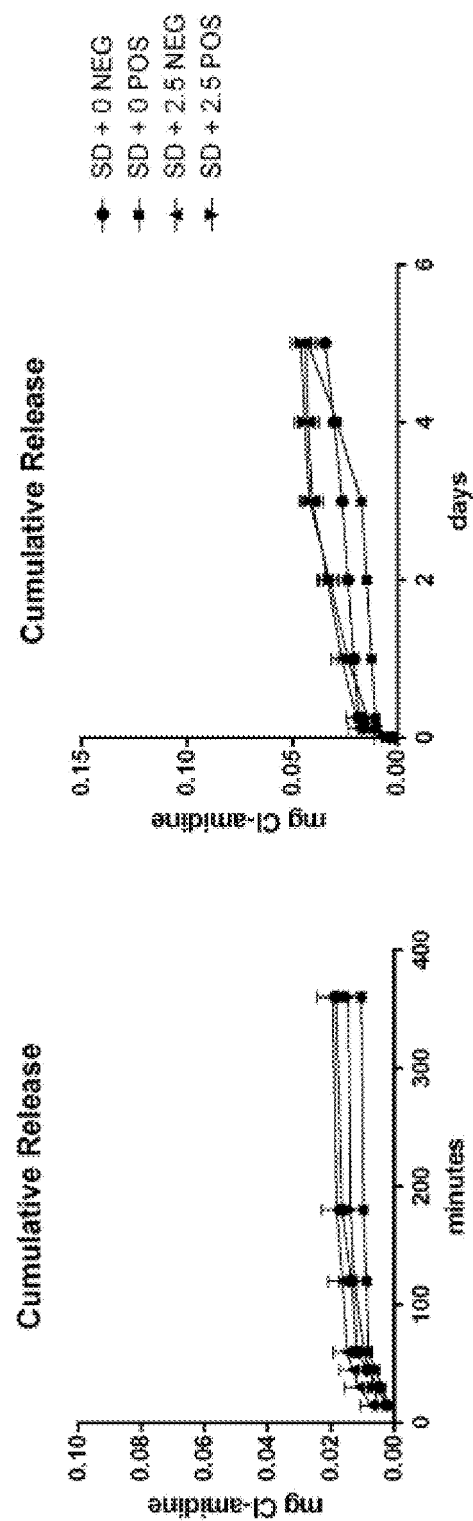
FIG. 21D
FIG. 21C

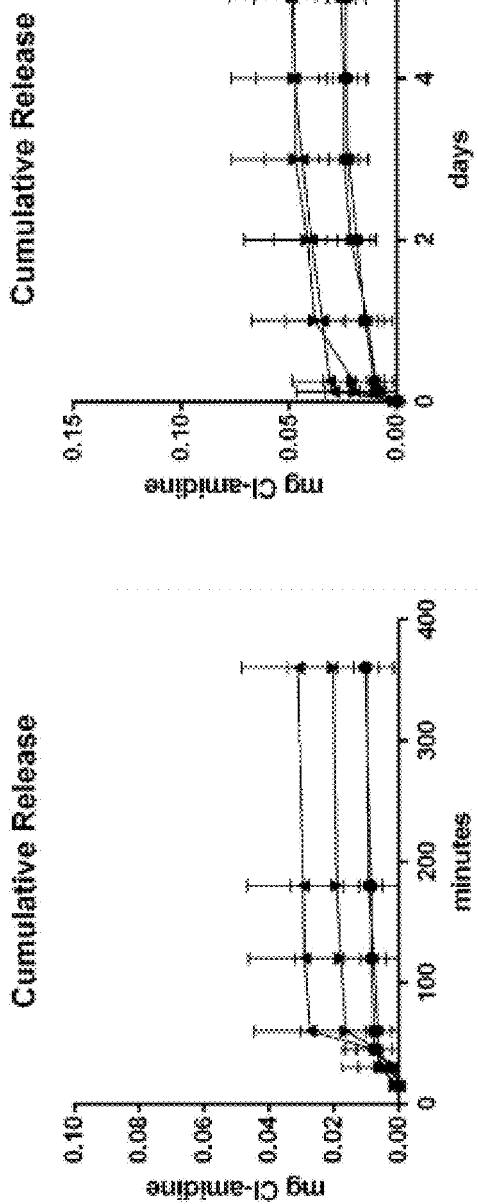
FIG. 22B
FIG. 22A
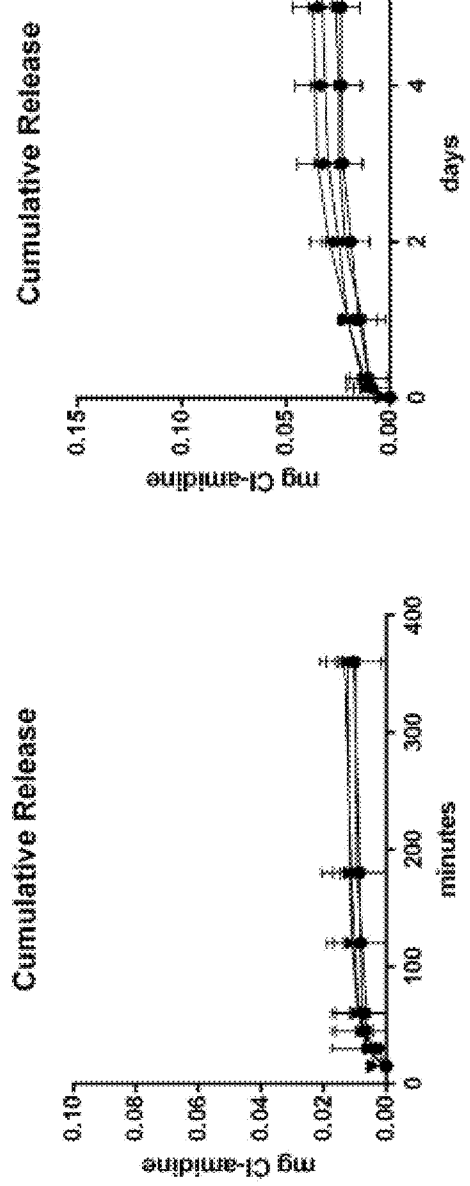
FIG. 22D
FIG. 22C

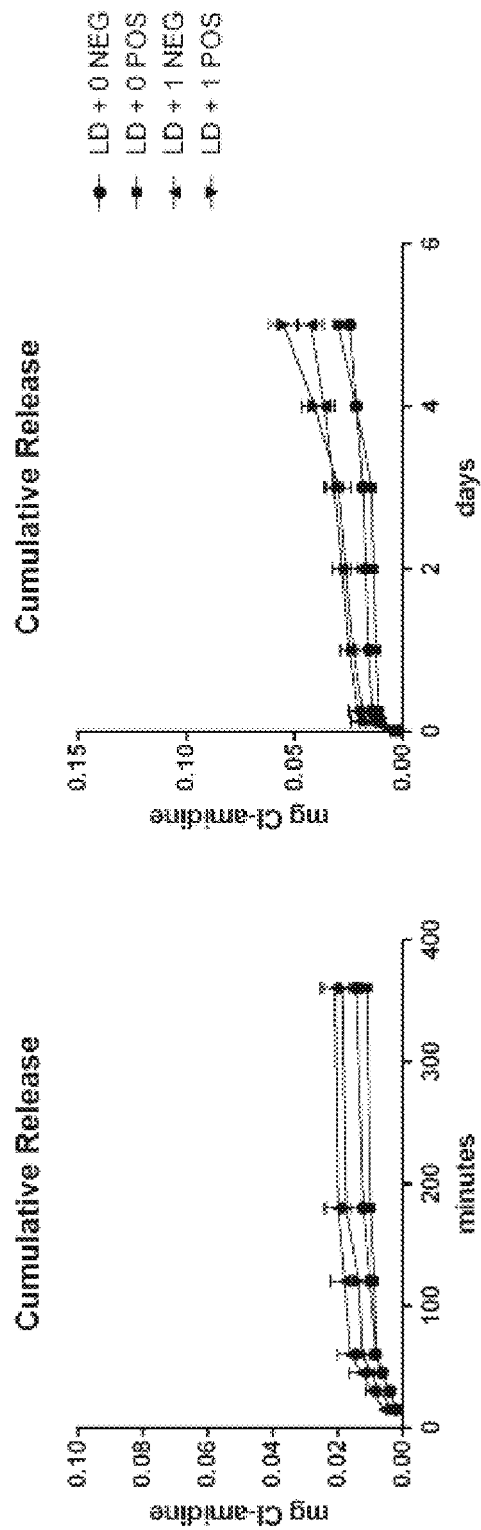
FIG. 23A
FIG. 23B
D
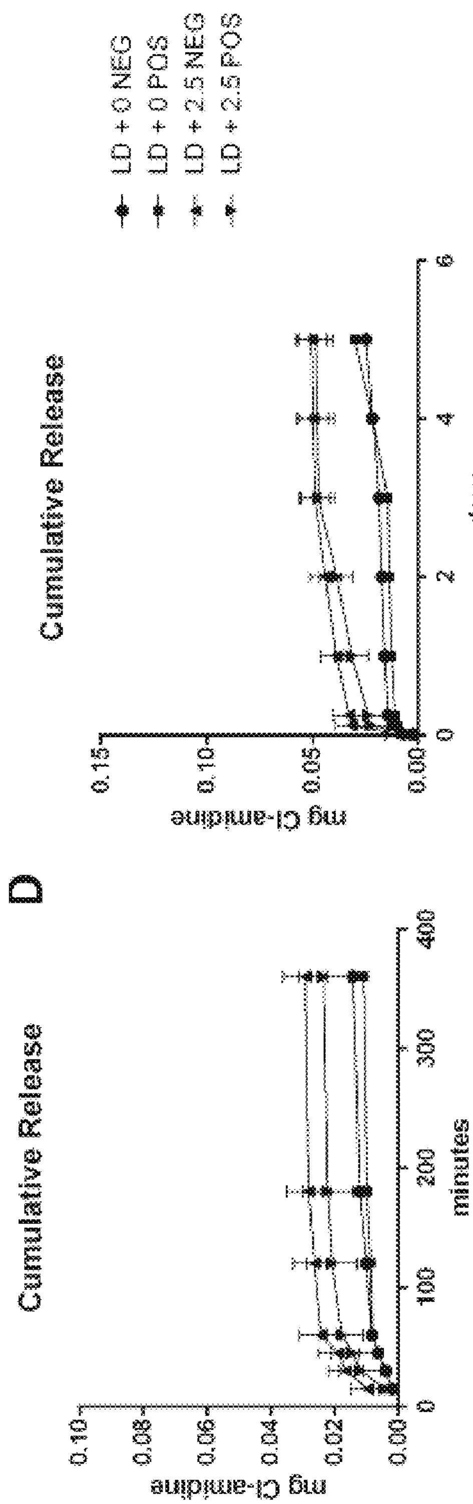
FIG. 23C
FIG. 23D

COMPOSITIONS AND METHODS FOR INHIBITING INFLAMMATION

CROSS-REFERENCE TO RELATED APPLICATIONS

This application claims the benefit of and priority to the following U.S. Provisional Application No. 62/641,146, filed Mar. 9, 2018, the entire contents of which are incorporated herein by reference.

STATEMENT OF RIGHTS TO INVENTIONS MADE UNDER FEDERALLY SPONSORED RESEARCH

This invention was made with government support under Grant Number R21EB024131 awarded by the National Institutes of Health. The government has certain rights in the invention.

BACKGROUND OF THE INVENTION

Neutrophils are the sentinels of the innate immune response. Unfortunately, neutrophil activation can sometimes result in chronic inflammatory and fibrotic responses that impair tissue repair and wound healing. Peptidyl arginine deiminases are intimately linked with the process of inflammation and its most vivid manifestation, the release of neutrophil extracellular traps (NETs). NETs, which consist of decondensed nuclear chromatin and granule components, have protective functions in an infection, but an excess of NETs leads to impaired wound healing and tissue damage. Chronic inflammation associated with NETs disrupts the regenerative process necessary for healing in the context of an acellular template. Methods for inhibiting inflammation surrounding an acellular template are urgently required.

SUMMARY OF THE INVENTION

As described below, the present invention features compositions and methods for inhibiting inflammation in connection with an acellular template (e.g., an electrospun template).

One aspect of the invention provides a biomaterial comprising an agent that inhibits NETosis. In some embodiments, the biomaterial is a bioresorbable polymer template.

Another aspect of the invention is an electrospun polydioxanone (PDO) template comprising an amount of N-α-benzoyl-N5-(2-chloro-1-iminoethyl)-L-ornithine amide (Cl-amidine).

Another aspect of the invention is a biomaterial vehicle comprising N-α-benzoyl-N5-(2-chloro-1-iminoethyl)-L-ornithine amide (Cl-amidine).

Another aspect of the invention is a method for inhibiting local inflammation surrounding a template, the method comprising implanting in a body a template comprising an amount of Cl-amidine sufficient to inhibit inflammation, thereby inhibiting inflammation.

Another method disclosed herein is directed to inhibiting fibrosis surrounding a template, the method comprising implanting in body a template comprising an amount of Cl-amidine sufficient to inhibit fibrosis, thereby inhibiting fibrosis.

Another aspect of the present invention is a method for inhibiting biomaterial surface conditioning NETosis, the method comprising implanting in a body a biomaterial comprising an amount of Cl-amidine sufficient to inhibit biomaterial surface conditioning NETosis, thereby inhibiting biomaterial surface NETosis.

Another aspect of the present invention is a method for inhibiting local NETosis surrounding a template, the method comprising implanting in the body a template comprising Cl-amidine, thereby inhibiting NETosis.

In yet another aspect of the invention, a method is disclosed for regulating the response of cells that are resident in or that arrive at the site of scaffold insertion, the method comprising contacting the cell with a template comprising Cl-amidine.

Another aspect of the present invention is a kit comprising an electrospun polydioxanone (PDO) template that comprises an amount of N-α-benzoyl-N5-(2-chloro-1-iminoethyl)-L-ornithine amide (Cl-amidine).

In some embodiments, the amount of Cl-amidine is sufficient to inhibit fibrosis. In some embodiments, the amount of Cl-amidine is sufficient to inhibit inflammation. In some embodiments, the amount of Cl-amidine is sufficient to inhibit a Peptidyl arginine deiminase. In still other embodiments, the amount of Cl-amidine is sufficient to inhibit PAD4. In some embodiments of the methods disclosed herein, the method involves contacting a site of trauma with the biomaterial of claim 1.

In one embodiment, the template is impregnated with an agent (e.g., N-α-benzoyl-N5-(2-chloro-1-iminoethyl)-L-ornithine amide (Cl-amidine or Cl—Am)) that inhibits a peptidyl arginine deiminase (e.g., PAD4).

NET Inhibition

PAD4 functions in triggering NET release. Cl-amidine has been shown to be effective in animal models at micromolar potencies to irreversibly inhibit PAD4. This has led to Cl-amidine becoming a widely regarded therapeutic agent for use in the reduction of NET formation and of the detrimental effects of NETosis in various diseases. As reported herein, in vitro data indicates that the degree of NETosis induced by neutrophils interacting with electrospun templates is regulated to a considerable extent by composition and architecture (fiber and pore diameter). Moreover, in vivo data supports this finding and demonstrates that excess NET induction by implanted acellular templates leads to chronic inflammation and fibrosis. Given this knowledge, the degree of NETosis (or the level to which templates precondition NETs) can be down-regulated by the timed release of Cl-amidine from the electrospun fibers.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant a peptide, nucleic acid molecule, small compound, or stimulus. Agents include, for example, coumate, light (e.g., blue light), doxycycline.

By "ameliorate" is meant decrease, suppress, attenuate, diminish, arrest, or stabilize the development or progression of a disease or disorder.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

By "biomaterial" as used herein refers to an immunomodulatory material that regulate the neutrophil interaction.

"Bioresorbable polymer template" refers to a dissolvable or degradable substrate derived from naturally occurring monomers (e.g., poly(lactic acid (PLA)) or polymers derived from synthetic monomers (e.g., polydioxanone (PDO)).

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include a failure in tissue regeneration. In one embodiment, the invention ameliorates a failure of enthesis regeneration.

By "effective amount" is meant the amount of a required to ameliorate the symptoms of a disease relative to an untreated patient. The effective amount of a cell, tissue or organ generated using a system of the invention is that amount needed for the therapeutic treatment of a disease. An effective amount varies depending upon the manner of administration, the age, body weight, and general health of the subject. Ultimately, the attending physician or veterinarian will decide the appropriate amount and dosage regimen. Such amount is referred to as an "effective" amount.

By "fibrosis" is meant excess fibrous tissue generated during a reparative or reactive process.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

The terms "isolated," "purified," or "biologically pure" refer to material that is free to varying degrees from components which normally accompany it as found in its native state.

"Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high-performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

"NETosis," as used herein, refers to an immunological response to microbial or chemical factors, wherein neutrophils produce web-like DNA structures call "neutrophil extracellular traps (NETs) coated in histones and proteins."

As used herein, "obtaining" as in "obtaining an agent" includes synthesizing, purchasing, or otherwise acquiring the agent.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 m/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 5A is a schematic illustrating the response to an electrospun template. FIG. 5B is a schematic illustrating the use of electrospun templates for the delivery of Cl-amidine (Cl—Am) to modulate acute, local inflammation induced by neutrophil extracellular traps.

FIG. 7A is a series of images of small diameter templates generated using different concentrations of Cl-amidine. FIG. 7B is a series of images of large diameter templates generated from solution comprising different concentrations of Cl-amidine.

FIG. 7C is a graph of the fiber diameters of small and large diameter templates generated from solution comprising different concentrations of Cl-amidine. FIG. 7C is a graph of pore diameters of small and large diameter templates generated from solution comprising different concentrations of Cl-amidine. * indicates a significant difference ($p<0.05$). (mean±std. dev., $n<250$ for fiber diameter analysis and $n=60$ for pore diameter analysis).

FIG. 8A is a graph showing the elution of Cl-amidine from 0 to 6 hours from small diameter templates generated from solution comprising different concentrations of Cl-amidine. FIG. 8B is a graph showing the elution of Cl-amidine from 0 to 6 hours from large diameter templates generated from solution comprising different concentrations of Cl-amidine. FIG. 8C is a graph showing the elution of Cl-amidine from 6 hours to 5 days from small diameter templates generated from solution comprising different concentrations of Cl-amidine. FIG. 8D is a graph showing the elution of Cl-amidine from 6 hours to 5 days from large diameter templates generated from solution comprising different concentrations of Cl-amidine.

FIG. 9A is a series of representative fluorescent micrographs of small diameter templates that indicate different degrees of NETosis based on drug content (scale bars=100 μm). FIG. 9B is a series of representative fluorescent micrographs of large diameter templates that indicate different degrees of NETosis based on drug content (scale bars=100 μm). DAPI staining is in the left column. SYTOX Green staining is represented in the middle column of images. Merged DAPI and SYTOX Green staining is shown in the right column for both FIGS. 9A and 9B.

FIG. 10A is a series of representative fluorescent micrographs of small diameter templates indicate different degrees of NETosis based on drug content (scale bars=100 μm). FIG. 10B is a series of representative fluorescent micrographs of large diameter templates that indicate different degrees of NETosis based on drug content (scale bars=100 μm). DAPI staining is in the left column. SYTOX Green staining is represented in the middle column of images. Merged DAPI and SYTOX Green staining is shown in the right column for both FIGS. 10A and 10B.

FIGS. 11 A and 11 B compare the effects of different diameter templates and Cl-amidine content on the degree of NETosis (scale bars=100 μm).

FIG. 12A is a graph showing the DAPI/SYTOX Green ratio for small and large diameter templates at 3 hours. FIG. 12B is a graph showing the DAPI/SYTOX Green ration for small and large diameter templates at 6 hours.

FIG. 15 provides an equation.

FIGS. 16A and 1B shows Cl-amidine elution from template. FIG. 16A is a graph showing the elution of Cl-amidine from small and large diameter fibers at 3 hours. FIG. 16B is a graph showing the elution of Cl-amidine from small and large diameter fibers at 6 hours.

FIG. 17A is a series of images of small diameter fibers with different concentrations of Cl-amidine. FIG. 17A is a series of images of large diameter fibers with different concentrations of Cl-amidine.

FIG. 19A is an SEM of an electrospun template with small diameter (SD) fibers. FIG. 19B is an SEM of an electrospun template with intermediate (INT) diameter fibers.

FIG. 19C is an SEM of an electrospun template with large diameter (LD) fibers. The scale bars=30 μm.

FIG. 20A is a graph of small diameter (SD) fibers electrospun with different concentrations (mg/ml) of Cl-amidine. FIG. 20B is a graph of intermediate diameter (INT) fibers electrospun with different concentrations (mg/ml) of Cl-amidine. FIG. 20A is a graph of large diameter (LD) fibers electrospun with different concentrations (mg/ml) of Cl-amidine. * indicates a significant difference from intermediate diameter and large diameter ($p<0.05$).  indicates a significant difference from small diameter and large diameter ($p<0.05$). * indicates a significant difference from small diameter and intermediate diameter ($p<0.05$). (mean±std. dev., n>150).

FIGS. 21A to 21F illustrate cumulative release of Cl-amidine from small diameter PDO templates. FIG. 21A is a graph showing the cumulative release of Cl-amidine from small diameter PDO templates electrospun from solution comprising 1 mg/ml of Cl-amidine. The Cl-amidine release is measured between 0 and 400 minutes after being placed in well with Hank's buffered salt solution (HBSS). FIG. 21B is a graph showing the cumulative release of Cl-amidine from small diameter PDO templates electrospun from solution comprising 1 mg/ml of Cl-amidine. The Cl-amidine release is measured between 0 and 5 days after the templates are placed in well with Hank's buffered salt solution (HBSS). FIG. 21C is a graph showing the cumulative release of Cl-amidine from small diameter PDO templates electrospun from solution comprising 2.5 mg/ml of Cl-amidine. The Cl-amidine release is measured between 0 and 400 minutes after being placed in well with Hank's buffered salt solution (HBSS). FIG. 21D is a graph showing the cumulative release of Cl-amidine from inter small mediate diameter PDO templates electrospun from solution comprising 2.5 mg/ml of Cl-amidine. The Cl-amidine release is measured between 0 and 5 days after being placed in well with Hank's buffered salt solution (HBSS). FIG. 21E is a graph showing the cumulative release of Cl-amidine from small diameter PDO templates electrospun from solution comprising 5 mg/ml of Cl-amidine. The Cl-amidine release is measured between 0 and 400 minutes after being placed in well with Hank's buffered salt solution (HBSS). FIG. 21F is a graph showing the cumulative release of Cl-amidine from small diameter PDO templates electrospun from solution comprising 5 mg/ml of Cl-amidine. The Cl-amidine release is measured between 0 and 5 days after being placed in well with Hank's buffered salt solution (HBSS). "NEG" refers to templates fabricated with negative applied voltages at each time point. "POS" refers to templates fabricated with positive applied voltages at each time point.

FIGS. 22A to 22F illustrate cumulative release of Cl-amidine from intermediate diameter PDO templates. FIG. 22A is a graph showing the cumulative release of Cl-amidine from intermediate diameter PDO templates electrospun from solution comprising 1 mg/ml of Cl-amidine. The Cl-amidine release is measured between 0 and 400 minutes after being placed in well with Hank's buffered salt solution (HBSS). FIG. 22B is a graph showing the cumulative release of Cl-amidine from intermediate diameter PDO templates electrospun from solution comprising 1 mg/ml of Cl-amidine. The Cl-amidine release is measured between 0 and 5 days after the templates are placed in well with Hank's buffered salt solution (HBSS). FIG. 22C is a graph showing the cumulative release of Cl-amidine from intermediate diameter PDO templates electrospun from solution comprising 2.5 mg/ml of Cl-amidine. The Cl-amidine release is measured between 0 and 400 minutes after being placed in well with Hank's buffered salt solution (HBSS). FIG. 22D is a graph showing the cumulative release of Cl-amidine from inter intermediate mediate diameter PDO templates electrospun from solution comprising 2.5 mg/ml of Cl-amidine. The Cl-amidine release is measured between 0 and 5 days after being placed in well with Hank's buffered salt solution (HBSS). FIG. 22E is a graph showing the cumulative release of Cl-amidine from intermediate diameter PDO templates electrospun from solution comprising 5 mg/ml of Cl-amidine. The Cl-amidine release is measured between 0 and 400 minutes after being placed in well with Hank's buffered salt solution (HBSS). FIG. 22F is a graph showing the cumulative release of Cl-amidine from intermediate diameter PDO templates electrospun from solution comprising 5 mg/ml of Cl-amidine. The Cl-amidine release is measured between 0 and 5 days after being placed in well with Hank's buffered salt solution (HBSS). "NEG" refers to templates fabricated with negative applied voltages at each time point. "POS" refers to templates fabricated with positive applied voltages at each time point.

FIGS. 23A to 23F illustrate cumulative release of Cl-amidine from large diameter PDO templates. FIG. 23A is a graph showing the cumulative release of Cl-amidine from large diameter PDO templates electrospun from solution comprising 1 mg/ml of Cl-amidine. The Cl-amidine release is measured between 0 and 400 minutes after being placed in well with Hank's buffered salt solution (HBSS). FIG. 23B is a graph showing the cumulative release of Cl-amidine from large diameter PDO templates electrospun from solution comprising 1 mg/ml of Cl-amidine. The Cl-amidine release is measured between 0 and 5 days after the templates are placed in well with Hank's buffered salt solution (HBSS). FIG. 23C is a graph showing the cumulative release of Cl-amidine from large diameter PDO templates electrospun from solution comprising 2.5 mg/ml of Cl-amidine. The Cl-amidine release is measured between 0 and 400 minutes after being placed in well with Hank's buffered salt solution (HBSS). FIG. 23D is a graph showing the cumulative release of Cl-amidine from inter large mediate diameter PDO templates electrospun from solution comprising 2.5 mg/ml of Cl-amidine. The Cl-amidine release is measured between 0 and 5 days after being placed in well with Hank's buffered salt solution (HBSS). FIG. 23E is a graph showing the cumulative release of Cl-amidine from large diameter PDO templates electrospun from solution comprising 5 mg/ml of Cl-amidine. The Cl-amidine release is measured between 0 and 400 minutes after being placed in well with Hank's buffered salt solution (HBSS). FIG. 23F is a graph showing the cumulative release of Cl-amidine from large diameter PDO templates electrospun from solution comprising 5 mg/ml of Cl-amidine. The Cl-amidine release is measured between 0 and 5 days after being placed in well with Hank's buffered salt solution (HBSS). "NEG" refers to templates fabricated with negative applied voltages at each time point. "POS" refers to templates fabricated with positive applied voltages at each time point.

FIG. 24A is a series of light microscopy images of small diameter templates with different amounts of Cl-amidine modulating neutrophil behavior in mice. FIG. 24B is a series of light microscopy images of large diameter templates with different amounts of Cl-amidine modulating neutrophil behavior in mice.

FIG. 25A is graph illustrating the presence surface DNA after administration of small and large diameter templates with Cl-amidine. FIG. 25B is a graph illustrating neutrophil invasion into the template. FIG. 25C is a graph illustrating neutrophil degeneration. *Significant difference ($p<0.05$). +Significant difference between SD and LD templates ($p<0.05$) (mean±std. dev., n=3).

DETAILED DESCRIPTION OF THE INVENTION

Figure 1:
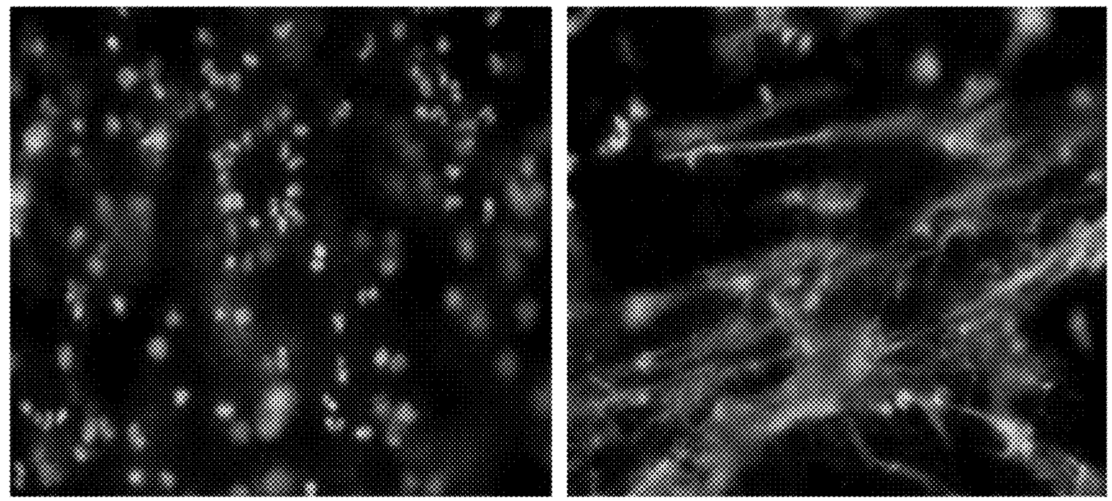
FIG. 1 is a series of representative images of neutrophils seeded on electrospun polydioxanone (PDO) (left large diameter, right small diameter) templates after 3 hours (both equal magnifications). Intact nuclei stain blue with DAPI, whereas extracellular chromatin emits SYTOX Green fluorescence.

As described below, the present invention features compositions and methods for the regulation of inflammation using a substrate (e.g., an electrospun template) impregnated with a PAD4 inhibitor for the spatiotemporally-controlled release of the PAD4 inhibitor.

NET Inhibition

Potentially the most critical aspect of biomaterial and tissue regeneration template design is to engineer material characteristics (i.e. electrospun template fiber and pore diameters) that elicit an innate immune response to drive tissue integration and regeneration as opposed to chronic inflammation and fibrosis. Since neutrophils are the first responder cells that interact with an implanted template, these cells direct the highly orchestrated wound healing response from initiation onward by preconditioning the device and microenvironment. NETs contribute to fighting infection as they assist to immobilize pathogens; however, excessive NETs are linked to delayed/impaired wound healing, chronic inflammation, and tissue damage. Thus, in order to achieve marginal tissue healing adjacent to the implanted template and enhance template tissue integration of the marginal tissue (in situ regeneration of acellular implants), templates are needed that regulate NETosis so as to reduce the potential for chronic inflammation while retaining the benefits of their antimicrobial activity. More broadly, neutrophils initiate the local inflammatory response, and, in analogy to M1 and M2 macrophages, neutrophils have the capacity to condition the microenvironment (N1 and N2). Down-regulating the degree of acute template-induced NET release favors the secretion of neutrophil factors that promote tissue healing and template integration, such as matrix metalloproteinase 9 (MMP-9), vascular endothelial growth factor, Interleukin 8 (IL-8).

NETs, web-like DNA structures coated in histones and proteins, are generated through NETosis in response to microbial or chemical factors and contribute to trap and kill pathogens. NETosis begins within minutes of activation with the citrullination of histones by PAD4, an enzyme localized in both cytoplasmic granules and the nucleus. Citrullination changes the charge of histones, resulting in chromatin decondensation and—following the breakdown of cellular membranes—the extrusion of the NETs into the extracellular space. The neutrophil response to implanted acellular tissue regeneration templates and biomaterials, and more importantly, the contribution of NETs to the success or failure of tissue templates remain complete unknowns. NETosis, first discovered in 2004, remains an understudied aspect of neutrophil biology. Not surprisingly, biomaterial scientists have generally ignored the potential and complex contribution of neutrophils to tissue implants. Furthermore, neutrophils release NETs when they are unable to phagocytose a foreign body, which may be considered synonymous to the formation of giant cells by fused, frustrated macrophages.

The present invention provides methods of treating disease and/or disorders or symptoms thereof that comprise providing to the patient a system to induce in vivo spatiotemporally regulated tissue regeneration or to provide to the patient an in vitro or ex vivo tissue regenerated using the compositions and/or methods of the invention. Thus, one embodiment is a method of treating a subject suffering from or susceptible to a defect in tissue regeneration or symptom thereof. The method includes the step of administering to the mammal a therapeutic amount of tissue or providing a system for tissue regeneration as described herein sufficient to treat the disease or disorder or symptom thereof, under conditions such that the disease or disorder is treated.

The methods herein include administering to the subject (including a subject identified as in need of such treatment) an effective amount of the compositions described herein (e.g., engineered cells, tissues, and electrospun templates) to produce spatiotemporally regulated tissue regeneration. Identifying a subject in need of such treatment can be in the judgment of a subject or a health care professional and can be subjective (e.g. opinion) or objective (e.g. measurable by a test or diagnostic method).

As used herein, the terms "treat," treating," "treatment," and the like refer to promoting tissue regeneration or otherwise regulating a biological process using the compositions and methods of the invention. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of a tissue or compositions described herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" is made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which defects in tissue regeneration or another biological process may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with defects in tissue regeneration or another biological process, in which the subject has been administered a therapeutic amount of a tissue or vector described herein as sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Templates (Also Termed "Scaffolds")

Electrospun materials possess a nanoscale fibrous structure that mimics the extracellular matrix (ECM) to support cell attachment and growth, and provides the advantage of having increased surface area for drug delivery. The nanofiber structure also results in interconnected porous structures, allowing communication between tissue compartments. This communication between cells is a vital component of the natural healing response, as chemotactic factors help native cells located in and around the site migrate into the template.

The invention provides a diverse set of agent-loaded templates. In one embodiment, an agent of the invention is used to control inflammation. In one embodiment, the template is loaded with an agent that inhibits inflammation (e.g., Cl-amidine). Both positive and negative polarities are applied to the electrospinning polymer solution, opposite a grounded collection mandrel, to create an electrical field driving force. In one embodiment, these parameters are optimized to modify the resultant drug-release profile of the template. Polymer concentration, which informs fiber diameter, is optimized to alter porosity, surface area to volume ratio (SAVR), and drug loading parameters.

In general, the materials of the invention comprise a biodegradable polymer and, if desired, a filler. A variety of biodegradable polymers are known in the art. In one embodiment, biodegradable polymers include proteins (such as gelatin and collagen), polymers derived from naturally-occurring monomers (such as poly(lactic acid (PLA)), and polymers derived from synthetic monomers (such as polydioxanone (PDO)). Desirably, biodegradable materials will degrade over a time period of less than a year, more preferably less than six months. In general, any biodegradable polymer that is biocompatible, and is shaped or formed into fibers and membranes, is employed in the present materials. Copolymers or mixtures/blends (multi-component) of biodegradable polymers can also be employed.

Other biocompatible polymers, some of which are biodegradable, include, but are not limited to, the following: poly(urethanes), poly(siloxanes) or silicones, poly(ethylene), poly(vinyl pyrrolidone), poly(-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate) (PVA), polyvinylhydroxide, poly(ethylene oxide) (PEO) and polyorthoesters or any other similar synthetic polymers that may be developed that are biologically compatible. Some preferred synthetic matrix materials include PEA, PGA, copolymers of PLA and PGA, polycaprolactone, poly(ethylene-co-vinyl acetate), (EVOH), PVA, and PEO. See also U.S. Pat. No. 7,374,774 (the contents of which is incorporated herein by reference in their entirety).

The term "filler", as used herein, refers to an organic or inorganic biocompatible material that provides structural reinforcement or rigidity to a polymer fiber, filament, or membrane. The filler may be a crystalline, a fiber, or a particle. Alternatively, the filler suitably has a shape of rod, fiber, sphere, oval, polyhedral crystal, and the like, however, the shape of the filler is not particularly limited thereto. The filler has an average diameter in nanoscale (nanofiller) ranging from about 1 nm to about 950 nm. The nanofiller suitably has an average diameter of about 1-100 nm, of about 10-80 nm, of about 25-75 nm, or particularly of about 50 nm. Alternatively, the filler has an average diameter in microscale (microfiller) that is greater than at least about 100 nm. The microfiller suitably has an average diameter of about less than about 10 micron, less than about 9 micron, less than about 8 micron, less than about 7 micron, less than about 6 micron, less than about 5 micron, less than about 4 micron, less than about 3 micron, less than about 2 micron, or particularly less than about 1 micron. For example, the filler is a nanocrystalline or fiber material and has an average diameter or thickness of less than about 100 nm, and advantageously may have an average length of less than about 500 nm. Advantageously, a nanofiller can possess an electrostatic charge, which may adhere to or attract growth factors when implanted or applied to a wound site.

Methods for Preparing Compositions

Compositions comprising a biodegradable polymer, a filler, and an agent is prepared by any suitable method, some of which are known in the art. In general, a filler is suspended or dispersed in a solvent (which will not substantially dissolve the filler) to form a dispersion or suspension; the biodegradable polymer and the agent are then mixed with the dispersion or suspension to form a composition of the invention. In certain embodiment, a therapeutically effective amount of agent is additionally added to the composition for enhancing regeneration. In certain embodiments, the solvent is 2,2,2-trifluoroethanol, 1,1,1,3,3,3-hexafluoro-2-propanol (HFP) or 9:1 acetic acid:water. The amount of solvent used should be minimized to facilitate electrospinning or other processing of the composition into fibers and membranes.

Methods for Preparing Fibers and Membranes

A composition comprising a biodegradable polymer, a filler, and an agent is used to prepare fibers and membranes by any suitable method, some of which are known in the art. In one embodiment, a fiber or membrane is formed by electrospinning Electrospinning is a known technique (see, e.g., Li et al., Biomaterials. 2005 October; 26(30):5999-6008.) and electrospinning apparatus is purchased commercially. For example, a charged solution comprising, for example, a biodegradable polymer is fed through a small opening or nozzle (usually a needle or pipette tip). Due to its charge, the solution is drawn toward a grounded collecting plate, e.g., a metal screen, plate, or rotating mandrel, typically 5-30 cm away, as a jet. During the jet's travel, the solvent gradually evaporates, and a charged fiber is left to accumulate on the grounded target. The charge on the fibers eventually dissipates into the surrounding environment. If the target is allowed to move with respect to the nozzle position, specific fiber orientations (aligned or random) is achieved.

The compositions of the invention are made as electrospun fiber compositions. In one embodiment, the invention provides a method of producing a membrane, the method comprising:

a) dispersing a filler in a solvent to form a dispersion;

b) combining a biodegradable polymer and an agent with the dispersion to form a composition; and c) electrospinning the composition to form fibers, thereby forming a membrane comprising a biodegradable polymer, a filler, and an effective amount of agent (e.g., Cl-amidine).

In certain embodiments, the filler is added to the composition, such that the step a) is omitted and the biodegradable polymer and agent is combined with the solvent to form a composition.

The method may further comprise adding at least one additional filler and at least one therapeutic agent before electrospinning. The electrospun membrane is formed in multiple layers. For example, the composition is additionally electrospun on top of one layer or other layers to create multiple-layer electrospun membrane.

In another embodiment, the solvent is removed from a dispersion comprising a biodegradable polymer, a filler, and an effective amount of agent to form a sponge. Solvent is removed by evaporation or lyophilization (freeze-drying). Thus, in one embodiment, the invention provides a method of producing a membrane. A membrane for use in the therapeutic methods of the invention should have sufficient rigidity to support the surrounding soft tissue, be malleable at its glass transition temperature (Tg) but regain rigidity on cooling (i.e. hold shape formed in situ), and be biocompatible in that it will promote tissue integration and not adversely affect the surrounding soft tissue.

The size and thickness of a membrane of the invention is varied according to the intended use. The membranes are spun to a desired size, or a sponge is cast to a desired size, followed by compression to a desired density and thickness. For example, barrier membranes are commonly between 0.1-0.4 mm in thickness, so the sponge can be suitably compressed to a thickness of about 0.1-0.4 mm.

The membrane can have any shape (round, square, rectangular, irregular). In exemplary embodiments, a membrane of the invention has a width from 1 to 20 mm and a length from 1 to 20 mm. In certain embodiments, a membrane is less than 1 mm in thickness, less than 0.5 mm thickness, less than 0.3 mm in thickness, or less than 100 microns in thickness.

Therapeutic and Prophylactic Applications

The present invention provides a ready supply of materials useful for promoting tissue regeneration and inhibiting inflammation. Compositions and materials of the invention are administered (e.g., directly or indirectly) to a damaged or diseased tissue or organ where they engraft and establish functional connections with a target tissue (e.g., bone, muscle, ligament, tendon). In one embodiment, a membrane of the invention enhances regeneration. Methods for repairing damaged tissue or organs may be carried out either in vitro, in vivo, or ex vivo. In another embodiment, the invention provides a method of promoting tissue regeneration, the method comprising contacting a tissue surface with a composition, fiber, compressed membrane, particulate, swelling membrane, non-compressed membrane or multiple-layer membrane (compressed or non-compressed) of the invention. In certain embodiments, the method is a method of promoting tissue regeneration after a surgical procedure (e.g., reconstructive surgery).

In another embodiment, the invention provides a method of promoting healing of a tissue defect, the method comprising contacting the tissue with a composition, fiber, compressed membrane, particulate, swelling membrane, non-compressed membrane or multiple-layer membrane (compressed or non-compressed) of the invention.

In still another embodiment, the invention provides a method of promoting soft tissue healing in a damaged tissue, the method comprising contacting the damaged tissue with a composition, fiber, membrane, particulate, swelling membrane, non-compressed membrane or multiple-layer membrane (compressed or non-compressed) of the invention.

In certain embodiments of the above aspects, the method is a method of promoting regeneration after a surgical procedure.

Administration

Compositions, fiber, and membranes of the invention can be provided directly to a tissue or organ of interest (e.g., by direct application to a bone or tissue surface, or by surgical implantation). A membrane can be applied to cover, surround, fill, or otherwise contact a tissue defect, wound, skin/wound healing, or surgical site. If desired, expansion and differentiation agents can be provided prior to, during or after administration of the composition, fiber, or membrane to increase, maintain, or enhance production or differentiation of cells in vivo, including cells from a subject's tissues or from any type of graft material/transplant, i.e., allogenic, xenogenic, alloplastic or genetically produced tissue. Compositions of the invention include pharmaceutical compositions. When administering a therapeutic composition or material of the present invention (e.g., a pharmaceutical composition), it will generally be formulated in a unit dosage form. Agents, including additional therapeutic agents can be applied to the fibers or incorporated within fibers during fabrication.

Formulations

Compositions, fibers, membranes, or multiple-layer membranes of the invention of the invention can be conveniently provided as sterile preparations. Such compositions may be in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "Remington's Pharmaceutical Science," 17th edition, 1985, the contents of which are incorporated herein by reference in their entirety, may be consulted to prepare suitable preparations, without undue experimentation.

In some embodiments, additives are added that enhance the stability and sterility of the compositions, including antimicrobial preservatives, antioxidants, chelating agents, and buffers. Prevention of the action of microorganisms can be ensured by various antibacterial and antifungal agents, for example, parabens, chlorobutanol, phenol, sorbic acid, and the like. The compositions can be isotonic, i.e., they can have the same osmotic pressure as blood and lacrimal fluid. The desired isotonicity of the compositions of this invention is accomplished in some embodiments of the present invention using sodium chloride, or other pharmaceutically acceptable agents such as dextrose, boric acid, sodium tartrate, propylene glycol, or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. In addition, silver salts can be used as thickening agents. See also U.S. Pat. Nos. 8,367,094; 8,173,151; and 7,998,498 (which are incorporated herein by reference). In some embodiments, the concentration of the thickener will depend upon the agent selected. Using an appropriate amount of thickener will achieve the selected viscosity. The choice of suitable carriers and other additives will depend, in some embodiments, on the exact route of administration and the nature of the particular dosage form, e.g., liquid dosage form (e.g., whether the composition is to be formulated into a solution, a suspension, gel or another liquid form, such as a time release form or liquid-filled form).

Glycerin or similar components can be added to the admixture to improve fiber and membrane flexibility.

Exemplary agents that may be delivered together with a composition, fiber, membrane, or multiple-layer membrane of the invention of the invention include, but are not limited to, antibiotics, analgesics, anticoagulants, immunosuppressants, the therapeutic substance is selected from the group consisting of anesthetics, hypnotics, sedatives, sleep inducers, antipsychotics, antidepressants, antiallergics, antianginal s, antiarthritics, antiasthmatics, antidiabetics, antidiarrheal drugs, anticonvulsants, antigout drugs, antihistamines, antipruritics, emetics, antiemetics, antispasmondics, appetite suppressants, neuroactive substances, neurotransmitter agonists, antagonists, receptor blockers, reuptake modulators, beta-adrenergic blockers, calcium channel blockers, disulfarim, muscle relaxants, analgesics, antipyretics, stimulants, anticholinesterase agents, parasympathomimetic agents, hormones, antithrombotics, thrombolytics, immunoglobulins, hormone agonists, hormone antagonists, vitamins, antineoplastics, antacids, digestants, laxatives, cathartics, antiseptics, diuretics, disinfectants, fungicides, ectoparasiticides, antiparasitics, heavy metals, heavy metal antagonists, chelating agents, alkaloids, salts, ions, autacoids, *digitalis*, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, antioxidants, anti-inflammatories, wound care products, antitumoral agents, antiangiogenic agents, antigenic agents, wound healing agents, plant extracts, growth factors, growth hormones, cytokines, immunoglobulins, emollients, humectants, anti-rejection drugs, spermicides, conditioners, antibacterial agents, antifungal agents, antiviral agents, tranquilizers, cholesterol-reducing drugs, antitussives, histamine-blocking drugs, and monoamine oxidase inhibitors.

Other agents include proteins such as any one or more of activin A, adrenomedullin, acidic FGF, basic fibroblast growth factor, angiogenin, angiopoietin-1, angiopoietin-2, angiopoietin-3, angiopoietin-4, angiostatin, angiotropin, angiotensin-2, bone morphogenic protein 1, 2, or 3, cadherin, collagen, colony stimulating factor (CSF), endothelial cell-derived growth factor, endoglin, endothelin, endostatin, endothelial cell growth inhibitor, endothelial cell-viability maintaining factor, ephrins, erythropoietin, hepatocyte growth factor, human growth hormone, TNF-alpha, TGF-beta, platelet derived endothelial cell growth factor (PD-ECGF), platelet derived endothelial growth factor (PDGF), insulin-like growth factor-1 or -2 (IGF), interleukin (IL)-1 or 8, FGF-5, fibronectin, granulocyte macrophage colony stimulating factor (GM-CSF), heart derived inhibitor of vascular cell proliferation, IFN-gamma, IFN-gamma, integrin receptor, LIF, leiomyoma-derived growth factor, MCP-1, macrophage-derived growth factor, monocyte-derived growth factor, MMP 2, MMP3, MMP9, neuropilin, neurothelin, nitric oxide donors, nitric oxide synthase (NOS), stem cell factor (SCF), VEGF-A, VEGF-B, VEGF-C, VEGF-D, VEGF-E, VEGF, and VEGF164. Other agents that may be delivered together with a cell of the invention include one or more of LIF, bone morphogenic protein (BMP), retinoic acid, trans-retinoic acid, dexamethasone, insulin, indomethacin, fibronectin, and/or 10% fetal bovine serum, or a derivative thereof. Other agents include small oligonucleotides, such as SiDNA or SiRNA, including at least a portion of sequences to a therapeutic target.

Those skilled in the art will recognize that the polymeric components of the compositions described herein should be selected to be chemically inert and will not affect the viability or efficacy of the cell as described in the present invention. This will present no problem to those skilled in chemical and pharmaceutical principles or will present problems can be readily avoided by reference to standard texts or by simple experiments (not involving undue experimentation), from this disclosure and the documents cited herein.

Dosages

A composition, fiber, or membrane of this invention can be applied or implanted in an amount effective to provide tissue regenerating properties. The skilled artisan can readily determine the amount of the composition, fiber, or membrane of the invention to be administered in methods of the invention. Of course, for any composition to be administered to an animal or human, and for any particular method of administration, it is preferred to determine therefore: toxicity, such as by determining the lethal dose and $LD_{50}$ in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

Delivery Methods

Compositions of the invention (e.g., templates comprising agents or cells) can be provided directly to a tissue or organ of interest, such as a tissue damaged from injury or disease. Compositions can be administered to subjects in need thereof by a variety of administration routes. Methods of administration, in some embodiments, practiced using any mode of administration that is medically acceptable. “Medically acceptable,” as used herein means any mode that produces effective levels of the active compounds without causing clinically unacceptable adverse effects. Such modes of administration include surgical engraftment or injection (e.g., intramuscular, intra-cardiac, intraocular, and intracerebroventricular).

Kits

Compositions, fibers, membranes, or multiple-layer membranes of some embodiments of invention are supplied along with additional reagents in a kit. The kits can include, in some embodiments, instructions for the preparation of a material (such as a membrane), a treatment regime, reagents, and equipment (test tubes, reaction vessels, needles, syringes, etc.). The instructions provided in a kit according to the invention are directed in some embodiments to suitable operational parameters in the form of a label or a separate insert.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Neutrophil NETosis Response to Electrospun PDO-Based Templates In Vitro The polymer polydioxanone (PDO) was used to generate a bioresorbable vascular prosthetic capable of acellular implantation and in situ arterial regeneration. PDO bioresorbable vascular grafts woven from PDO sutures, alone or blended with natural polymers, allows for the electrospinning of seamless tubular prosthetics which possess mechanical properties that mimic the native arteries. The degradation rate is on the order of 6-8 weeks (13% original tensile strength at 8 weeks, which appears to be the key window for vascular in situ regeneration based on rat aortic replacement model evaluations (16-week implants).

Figure 2:
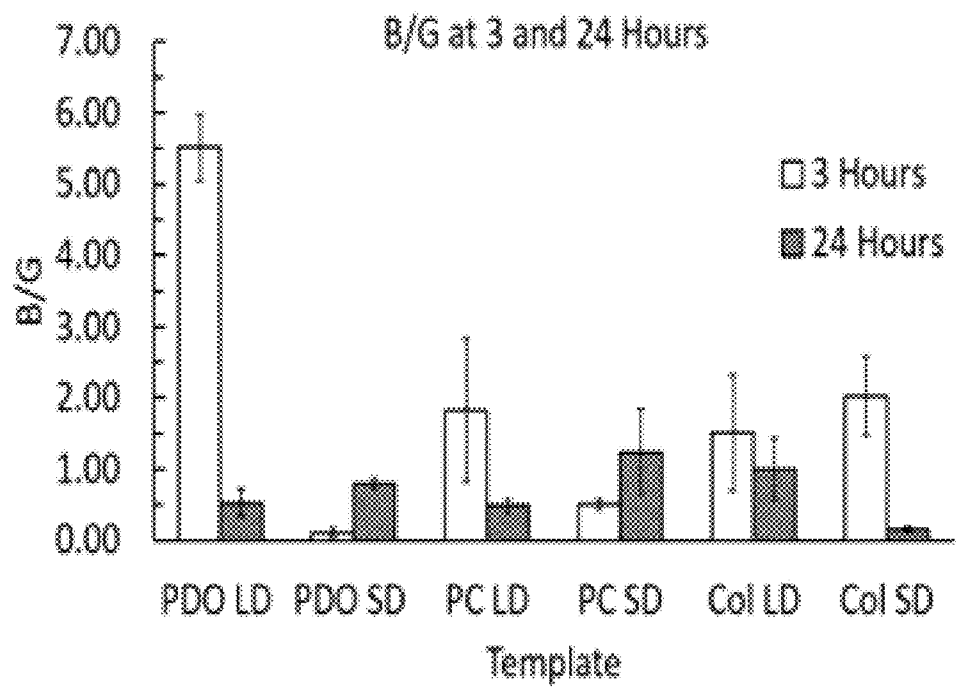
FIG. 2. Ratio of Blue/Green (B/G) area for neutrophils seeded on templates after 3 and 24 hours. "PDO" refers to polydioxanone. "LD" refers to large diameter. "SD" refers to small diameter. "Col" refers to collagen.

Neutrophil NETosis was evaluated on electrospun PDO, collagen type I (COL), and PDO/COL (PC, 90:10 v/v) blends produced at large (LD, 1.3±0.6 μm) and small (SD, 0.2±0.07 μm) fiber diameters. Fresh, non-activated, human peripheral blood neutrophils were isolated and seeded at $0.75 \times 0^6$ cells/well on 10 mm discs of the templates to evaluate the acute induction of NETs at 3 and 24-hour interactions. After each time period, the formalin-fixed seeded templates were stained for intact cell nuclei (4',6-diamidino-2-phenylindole (DAPI)) and NETs (SYTOX® Green nucleic acid stain (SG)). Template surfaces were analyzed by fluorescent microscopy (FIG. 1) to obtain the percent area representing intact nuclei (blue) versus percent area representing NETs (green) using ImageJ. The percentage of blue (B) area and the percentage of green (G) area were converted to a ratio of cell nuclei/NETs (FIG. 2) with a B/G ratio greater than 1 representing a larger template surface area covered by more intact nuclei than NETs. The overriding results were that the small diameter templates induced a significantly ($p<0.05$) higher degree of NETs while the large diameter templates trended toward less or a slower induction of NETs (contrasted in FIG. 1). This result indicates that the small diameter templates induced more NETosis, which may be more inflammatory. The inclusion of collagen tempers the response as compared to synthetic fibers alone. Because the neutrophils are not exhibiting NETosis at an early time point on large diameter fibers, large diameter templates may be more conducive for regeneration, as well as slow the onset of an inflammatory response. NETs are highly delicate DNA structures that are easily degraded, damaged, or detached from a surface. It is likely a large percentage of the NETs present at 3 hours degraded prior to fixing the scaffolds at 24 hours (poorer quality images for quantification). Additionally, a first step in NETosis is that the disintegration of nuclei. Interestingly, it was observed that the PDO large diameter surface at 3 hours is comprised mainly of banded neutrophils, which are maintained to a high percentage at 24 hours. The opposite is true for PDO small diameter, for which the vast majority of neutrophils with intact nuclei visible at 3 hours have lost a well-defined, banded nucleus.

Example 2: Neutrophil NETosis Response to Electrospun PDO Templates In Vivo

The electrospun PDO large diameter and small diameter templates described herein were implanted subcutaneously (10 mm punches, 500 μm thick, peracetic acid sterilized) in Sprague-Dawley rats to evaluate the in vivo template-induced NETosis. The study was designed to evaluate early-stage NET formation and host response (1, 2, and 7-day implant periods) as well as draw any correlation with the in vitro data. Upon retrieval, the 1 and 2-day samples (not integrated with marginal tissue) were processed for histone H3 (bound to extruded NETs) in situ quantification via a previously utilized On-cell Western assay (Odyssey® CLx Infrared Imaging System). Additionally, template sections were stained with DAPI and SG for evaluation of the degree of NETosis using a standard protocol. Of note, the 7-day samples were excised with surrounding tissue due to significant tissue integration into the large diameter (completely integrated in marginal tissue) more so than small diameter samples (only slight/spotty integration). The 7-day samples were processed (Hematoxylin and Eosin (H&E), SG, and DAPI) to examine the level of NETs present and the general host response correlated to the early-stage degree of NETosis.

Figure 3:
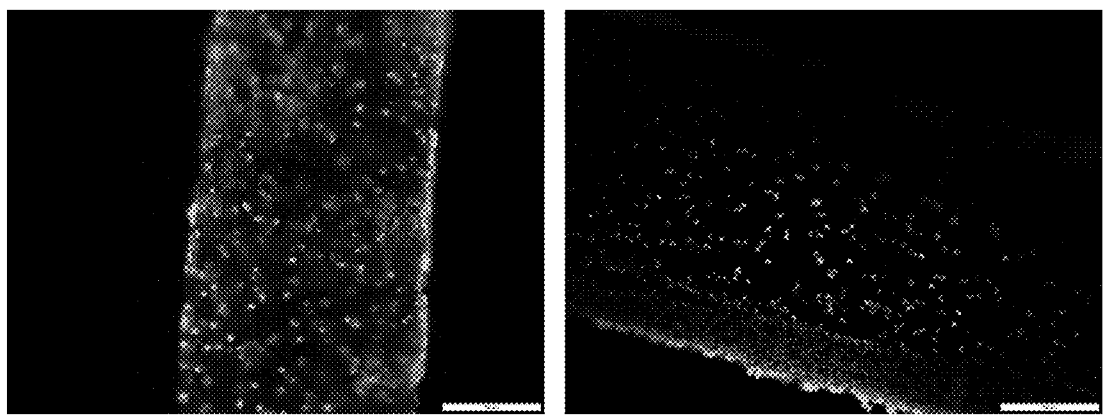
FIG. 3 is a series of representative SYTOX Green/DAPI stained images of electrospun PDO (left large diameter, right small diameter) templates after 24 hours in vivo (scale bar=100 μm).
Figure 4:
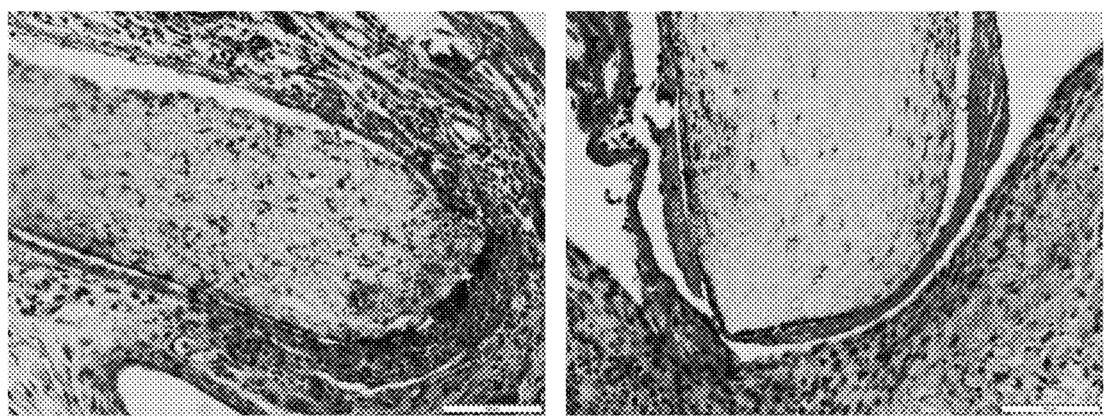
FIG. 4 is a series of representative images of electrospun PDO (left large diameter, right small diameter) templates Hematoxylin and Eosin (H&E) stained after 7 days in vivo (scale bar=100 μm)

The results indicated that the PDO small diameter templates at 24 hours had significantly ($p<0.05$) more template-bound histone H3 (2592±208 ng/cm$^2$) when compared to the PDO large diameter (1375±195 ng/cm$^2$). At 48 hours, the PDO small diameter and large diameter templates had equivalent histone H3 values (1395±10 and 1875±660 ng/cm$^2$, respectively) with the PDO small diameter having significantly less (almost half) from 24 hours. The SG/DAPI sections (FIG. 3) show distinct differences, whereas the PDO large diameter templates possess a migration and distribution of cells with minimal NETs throughout the template and the PDO small diameter templates maintain a distinct coating of cells with an increased NET presence and minimal cell migration through the template. As with the histone H3 and SG/DAPI data, the H&E sections showed that the PDO large diameter templates demonstrating significant marginal tissue integration (fibroblast infiltration across the template and hyper-cellular at the margin), minimal inflammation, and no fibrosis (FIG. 4). In contrast, the PDO small diameter samples had a high level of inflammatory cells present at the surface and throughout the template, no marginal tissue integration, and a well-developed fibrotic capsule. Thus, there appears to be a correlation between the degree of NETosis and the host response with the small diameter templates invoking higher NETosis and inflammation with no tissue integration/regeneration.

In summary, the in vitro and in vivo results are consistent and illustrate that the response is template-dependent and regulated by the template architecture.

Example 3: Cl—Amidine Activity is Retained after Solvent Exposure

Figure 5A:
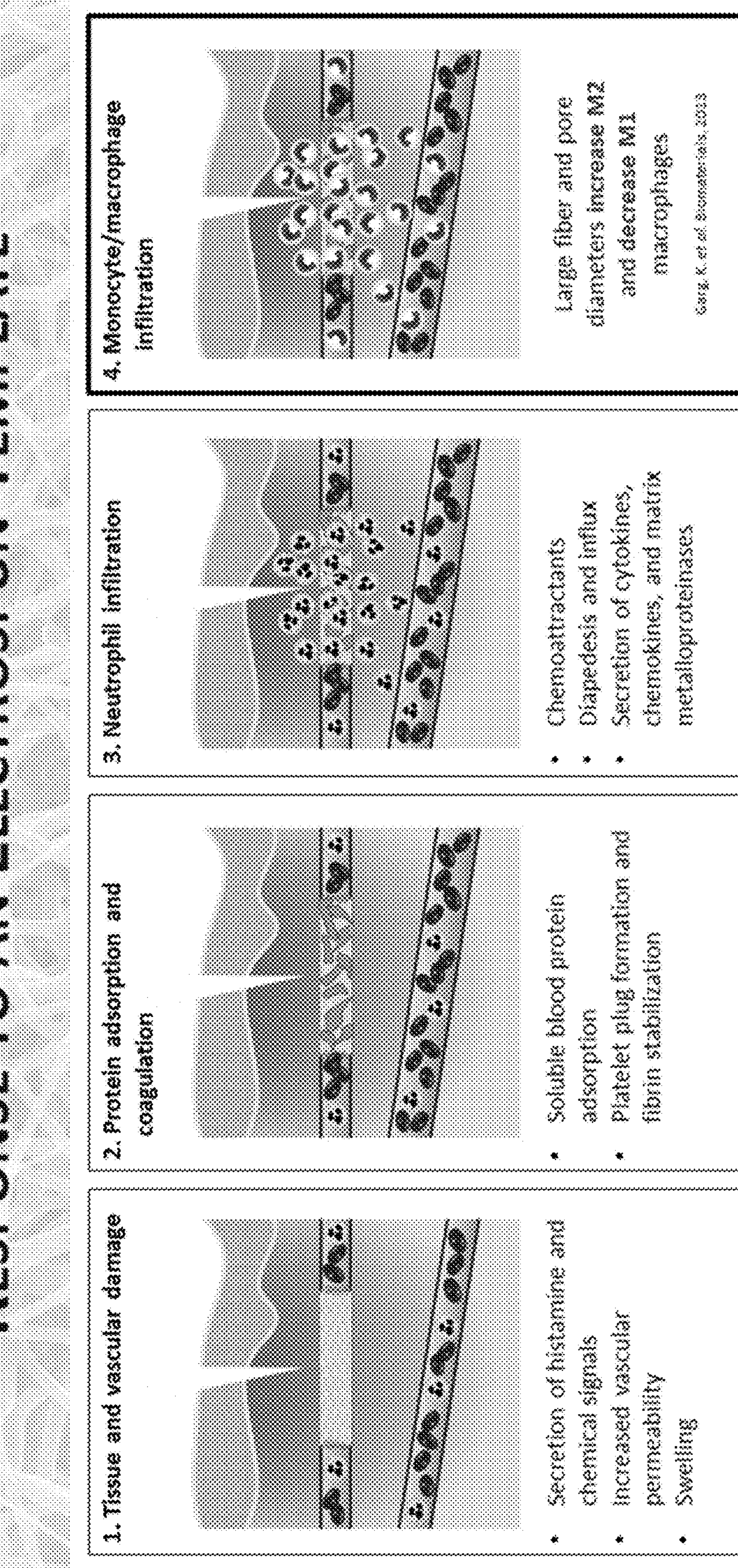
FIGS. 5A and 5B are schematics illustrating the invention.
Figure 5B:
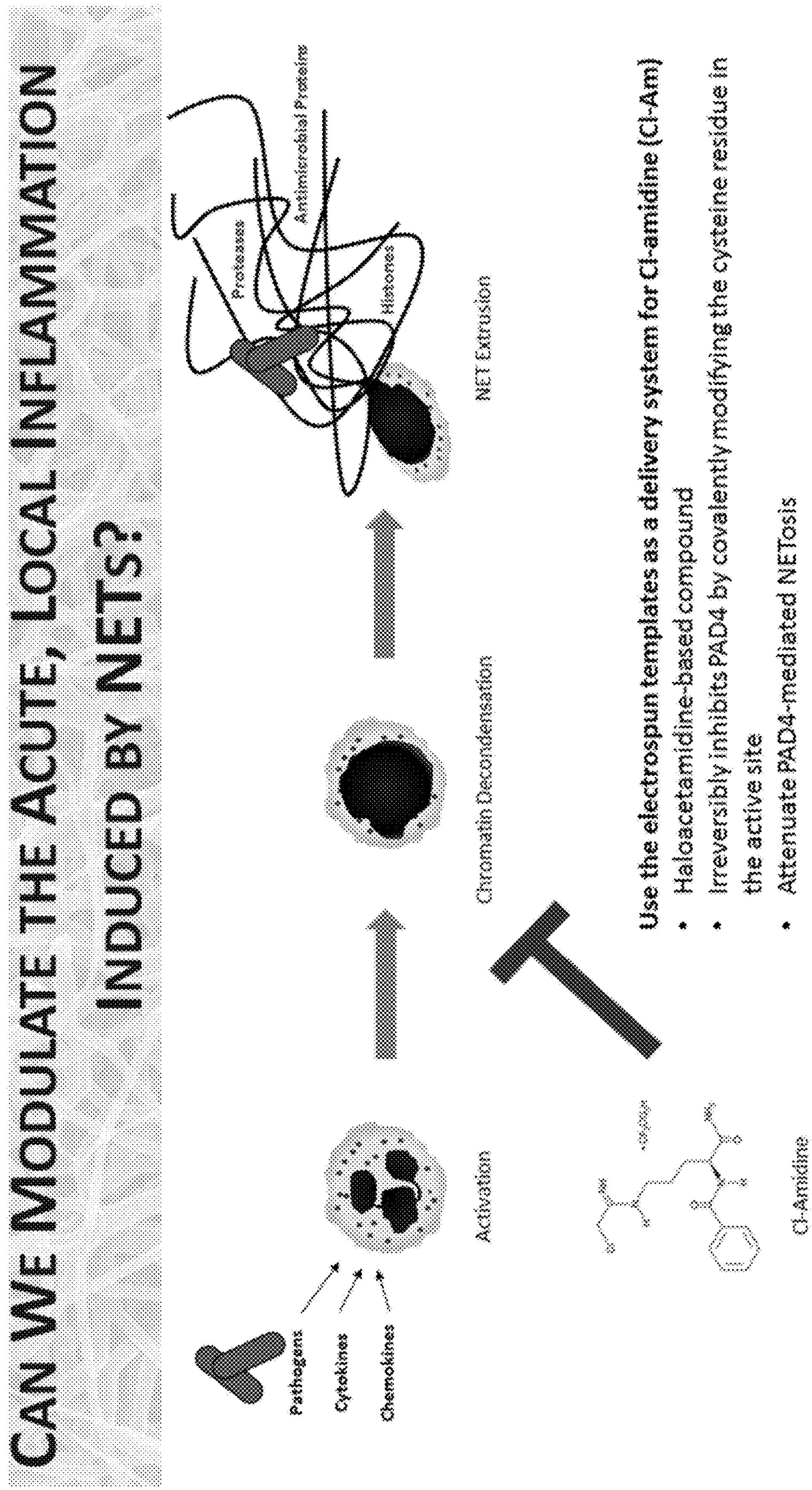

The incorporation of Cl-amidine into templates was tested. This technology can be tailored to obtain successful in situ, neutrophil-guided template integration and regeneration. Both in vitro and in vivo preliminary results indicate that the large fiber diameter and/or large pore size templates induced a lower degree of NETosis that is more conducive to tissue template integration, angiogenesis, and tissue regeneration (FIG. 5A). Additionally, the degree of NETosis may be attenuated by eluting Cl-amidine to accelerate tissue integration and healing beyond what is possible with template architecture and composition alone (FIG. 5B).

Figure 6:
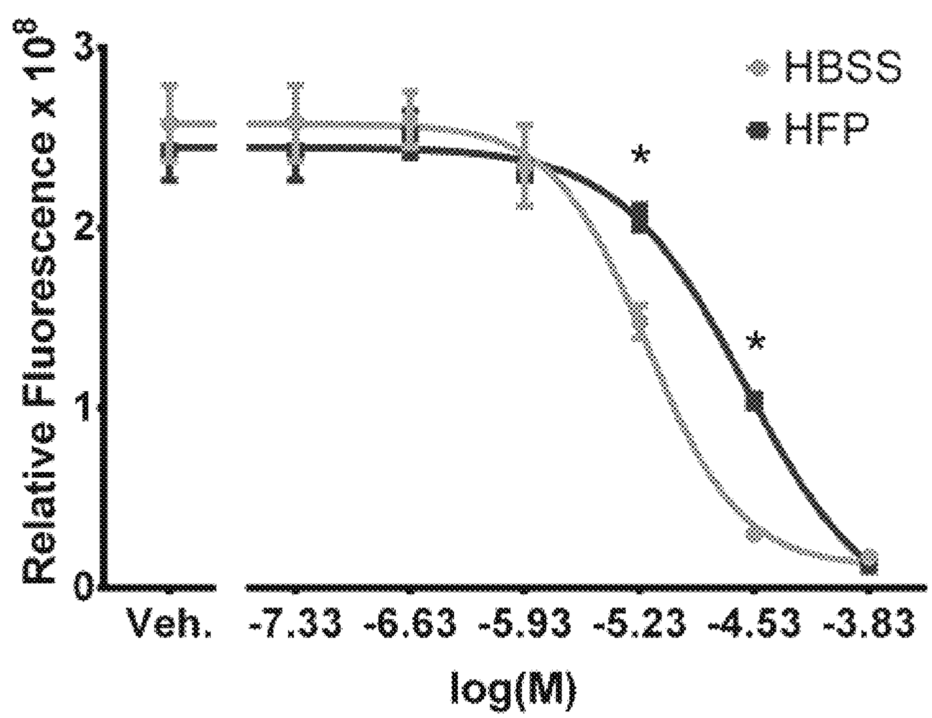
FIG. 6 is a graph quantitating relative fluorescence vs. Cl-amidine concentration.

The activity of Cl-amidine after solvent exposure was evaluated. 0 to 147.8 μM Cl-amidine (n=4) was exposed to the electrospinning solvent 1,1,1,3,3,3-hexafluoro-2-propanol (HFP). Standards of 0 to 147.8 μM Cl-amidine (n=4) in 1× Hank's buffered salt solution (HBSS) were created and the Cl-amidine activity was quantified after exposure with a PAD4 Inhibitor Screening Assay. The log transform of molarity against average fluorescent intensity was plotted for each concentration (FIG. 6).

Example 4: Template Fabrication and Characterization

Figure 7A:
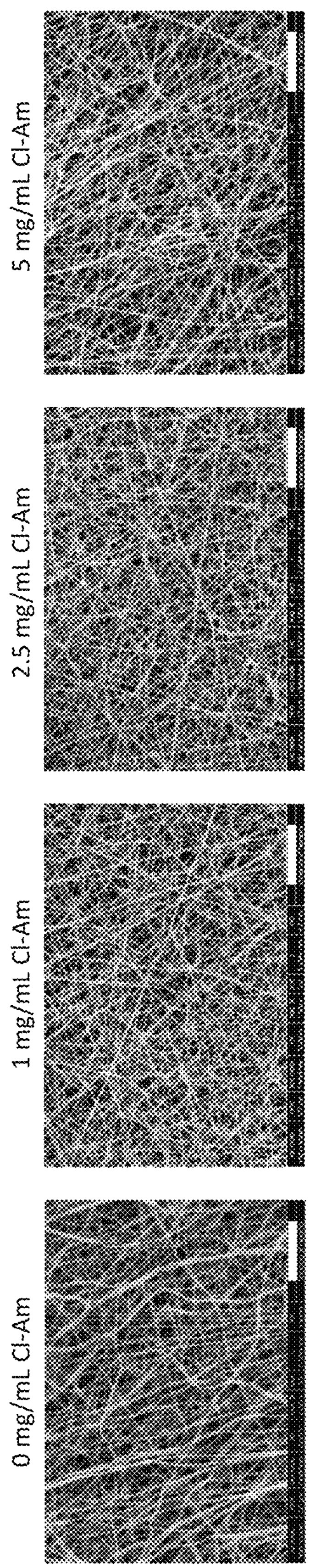
FIGS. 7A, 7B, 7C and 7D provide an analysis of template characteristics where the template incorporates Cl-amidine.
Figure 7B:
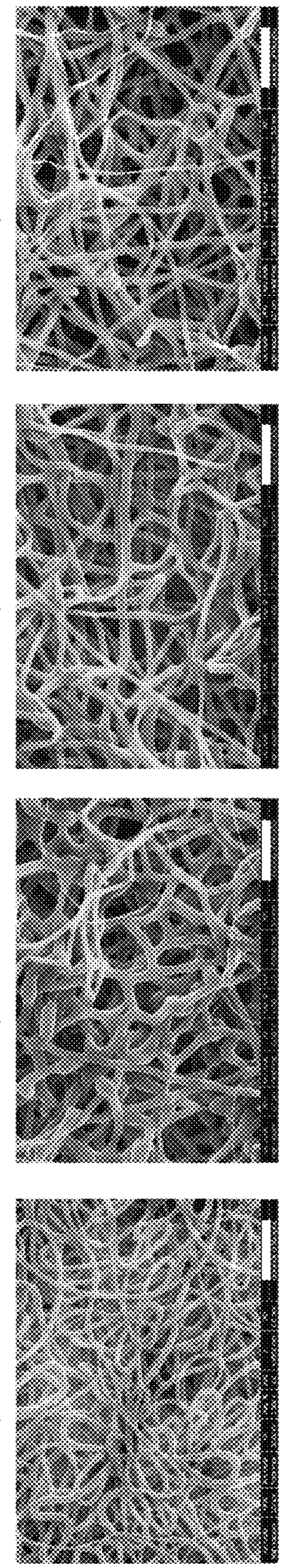
Figures 7C, 7D:
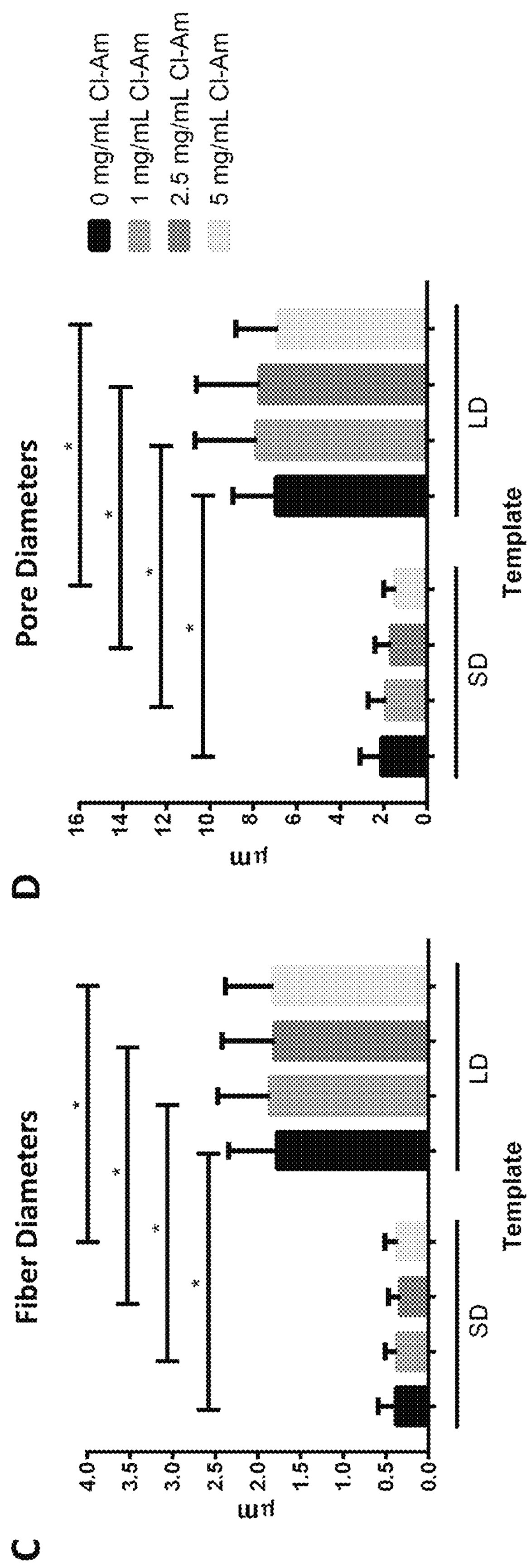
Figure 8A:
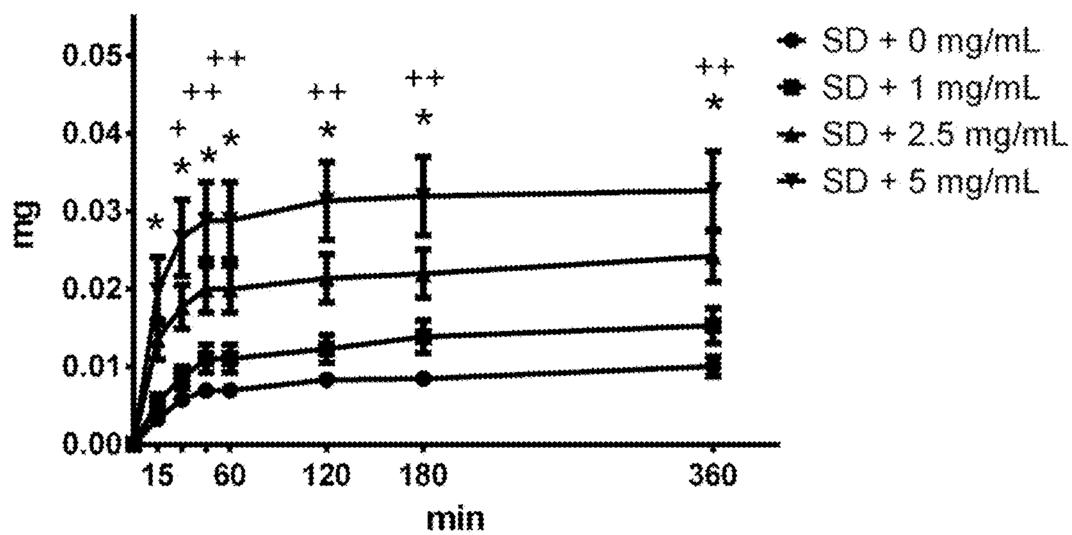
FIGS. 8A to 8D are illustrate Cl-amidine elution over time.
Figure 8B:
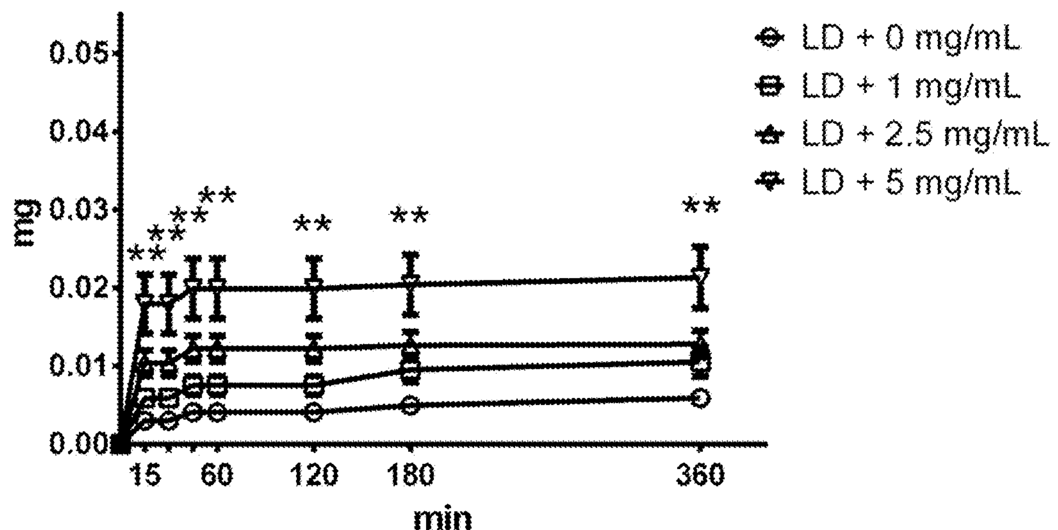
Figure 8C:
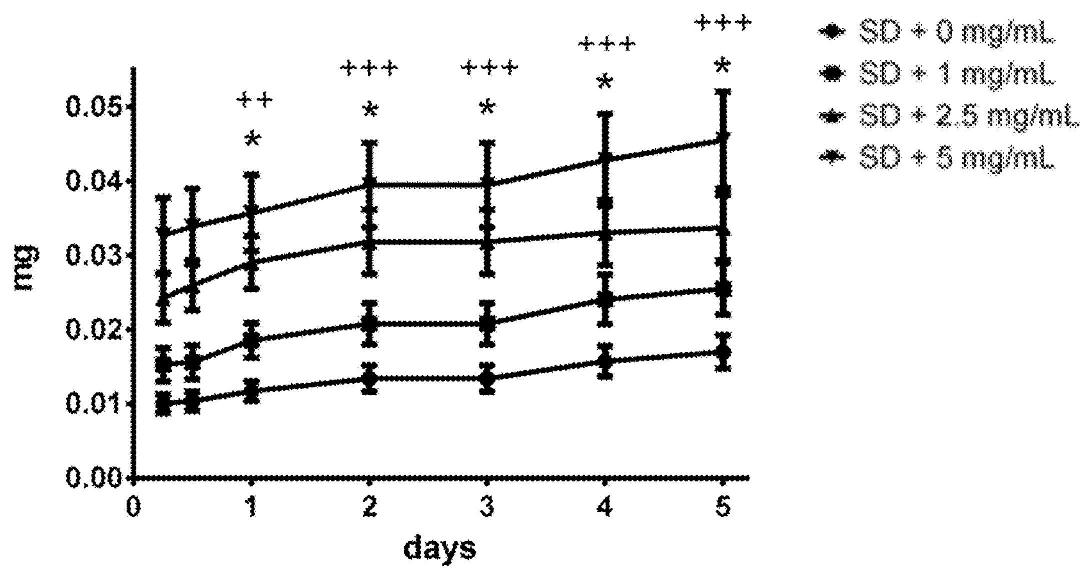
Figure 8D:
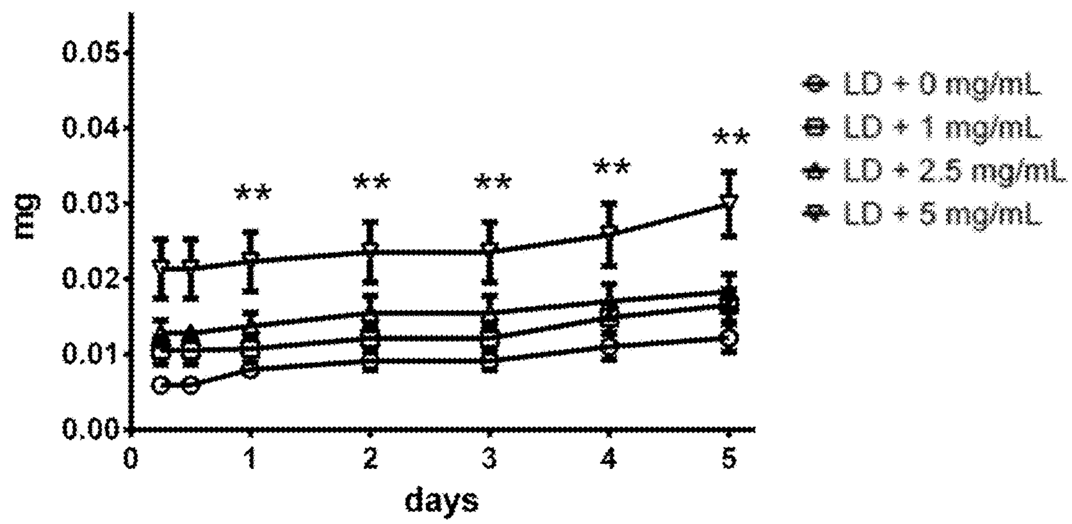
Figure 9A:
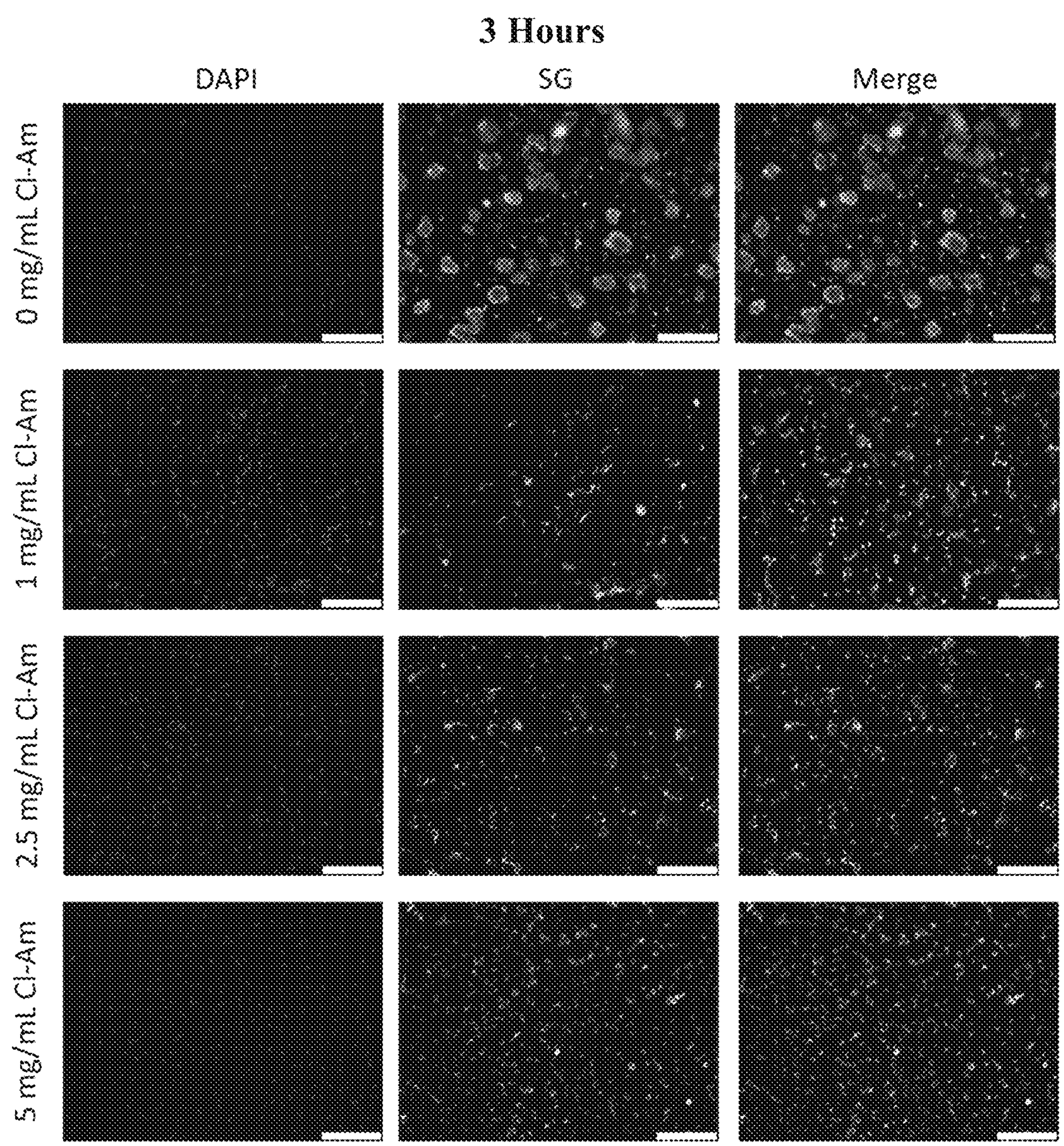
FIGS. 9A and 9B provide a series of fluorescent micrographs taken at 3 hours.
Figure 9B:
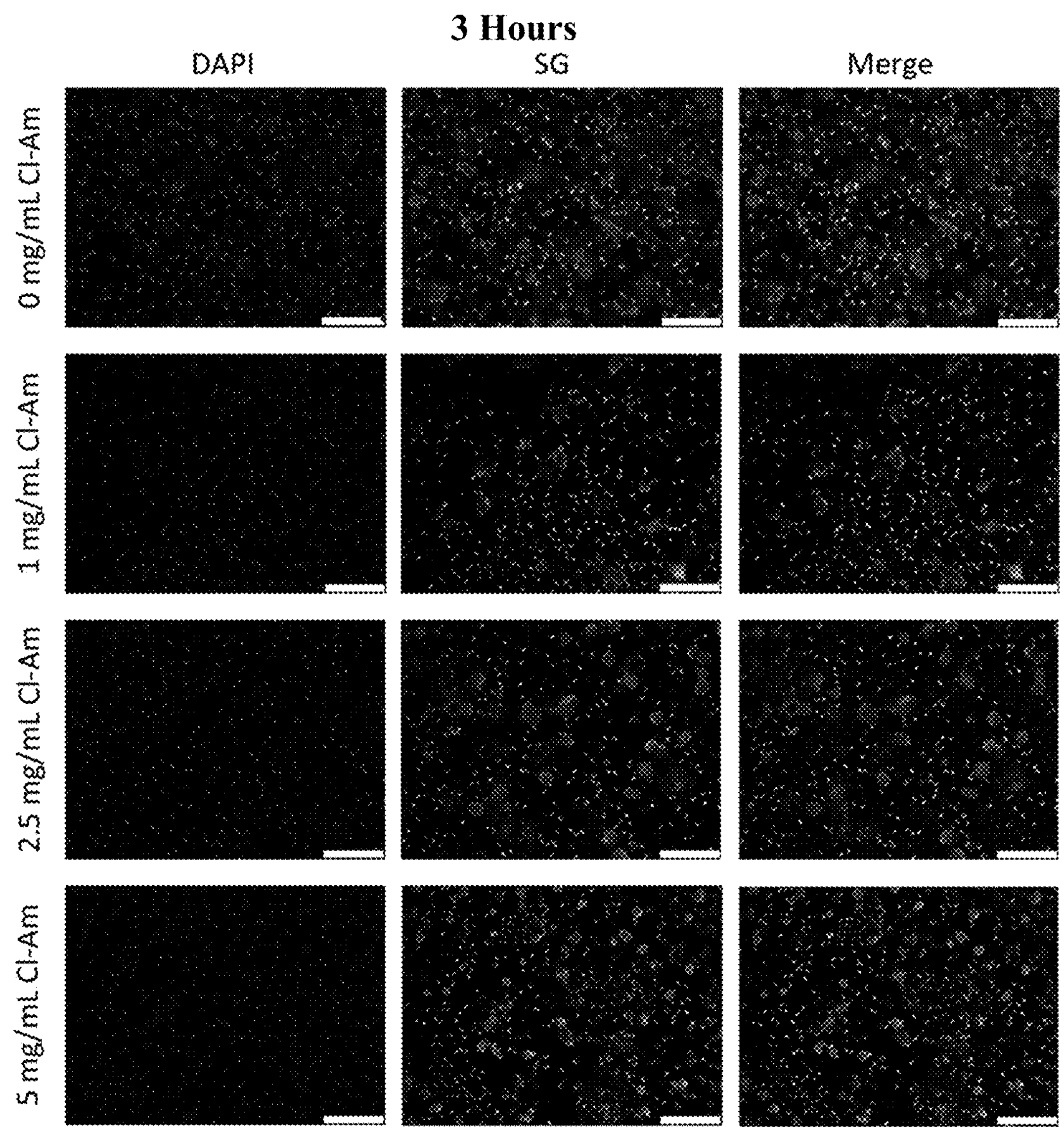
Figure 10A:
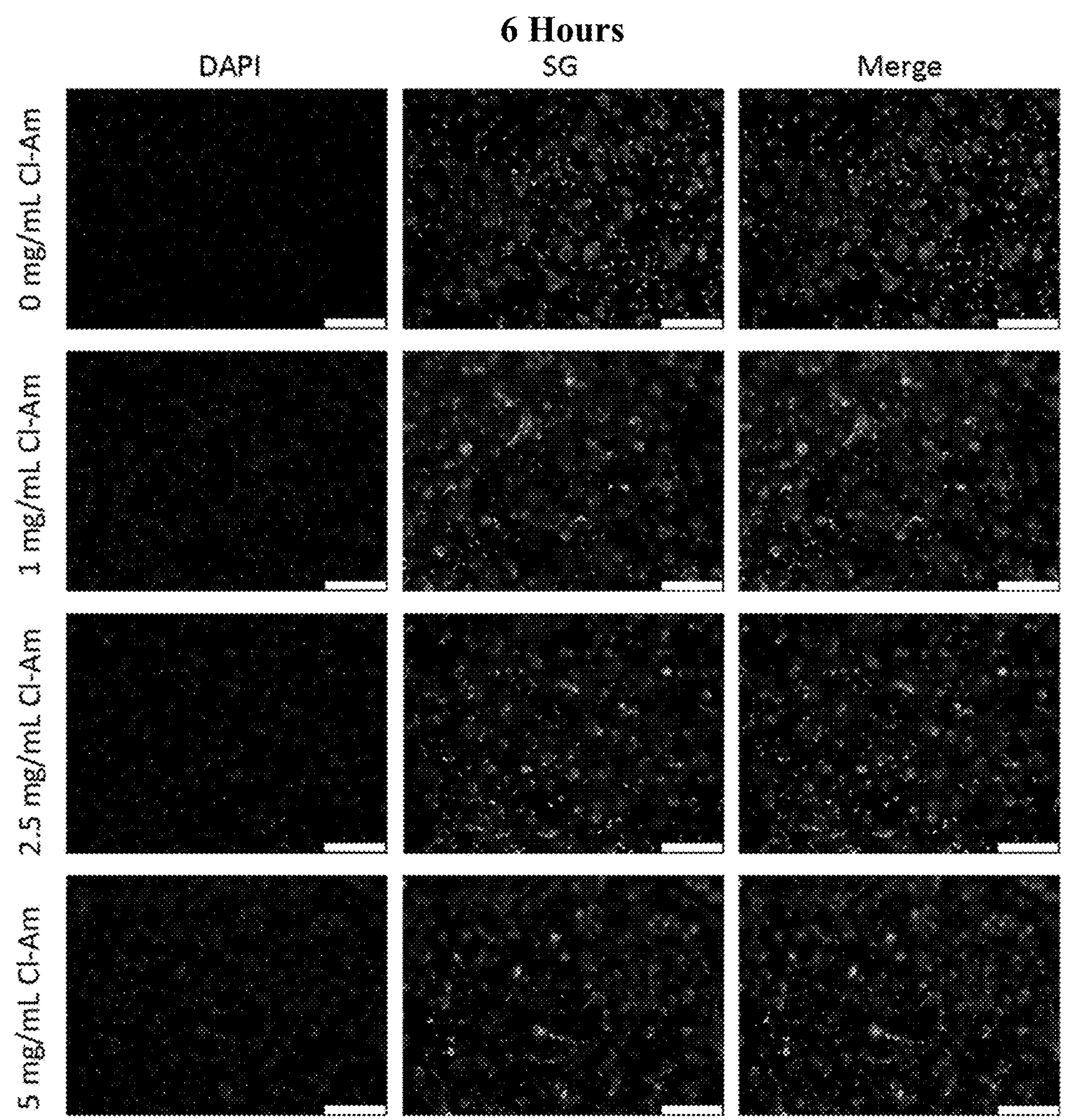
FIGS. 10A and 10B provide a series of fluorescent micrographs taken at 6 hours.
Figure 10B:
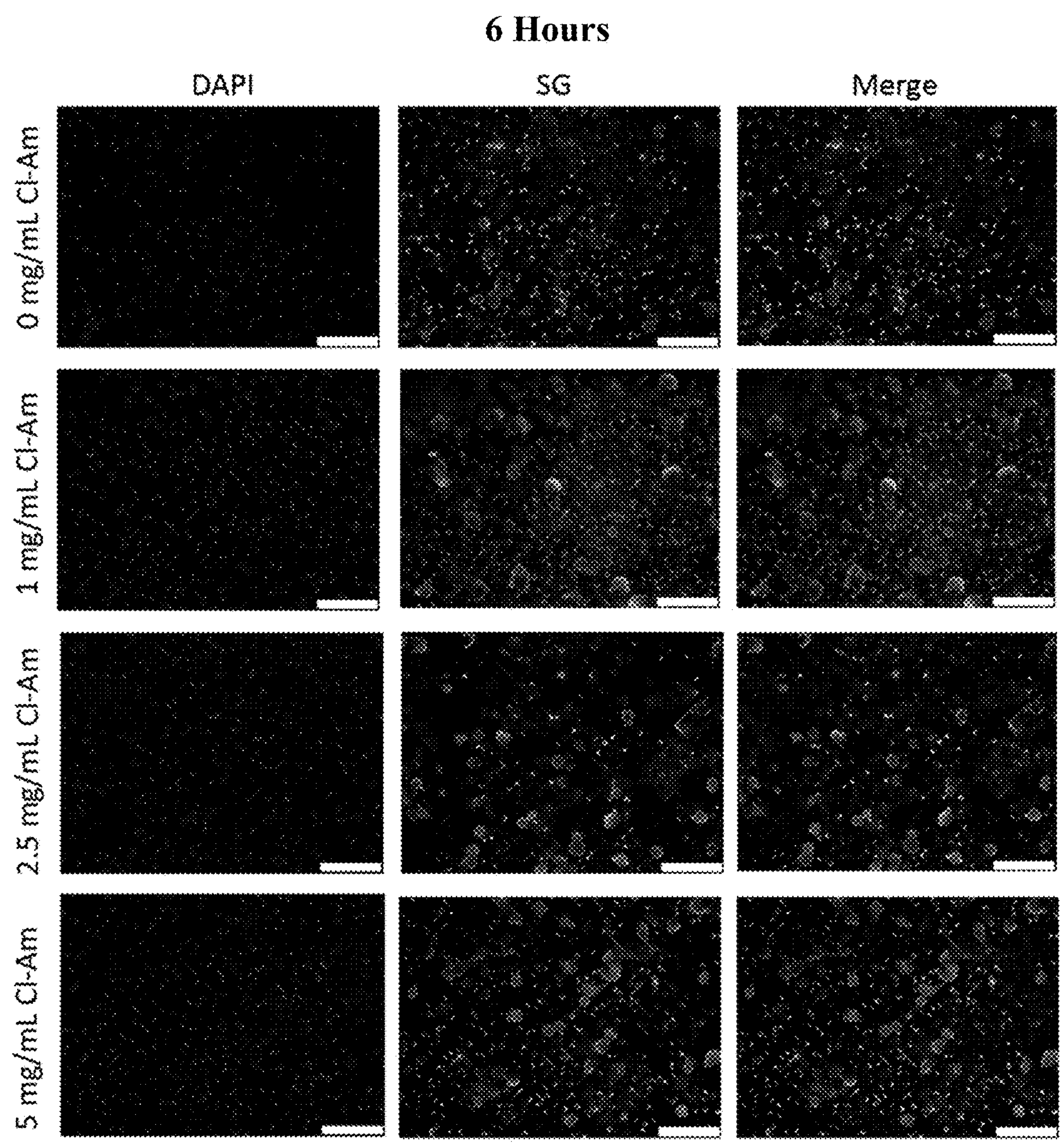
Figure 11A:
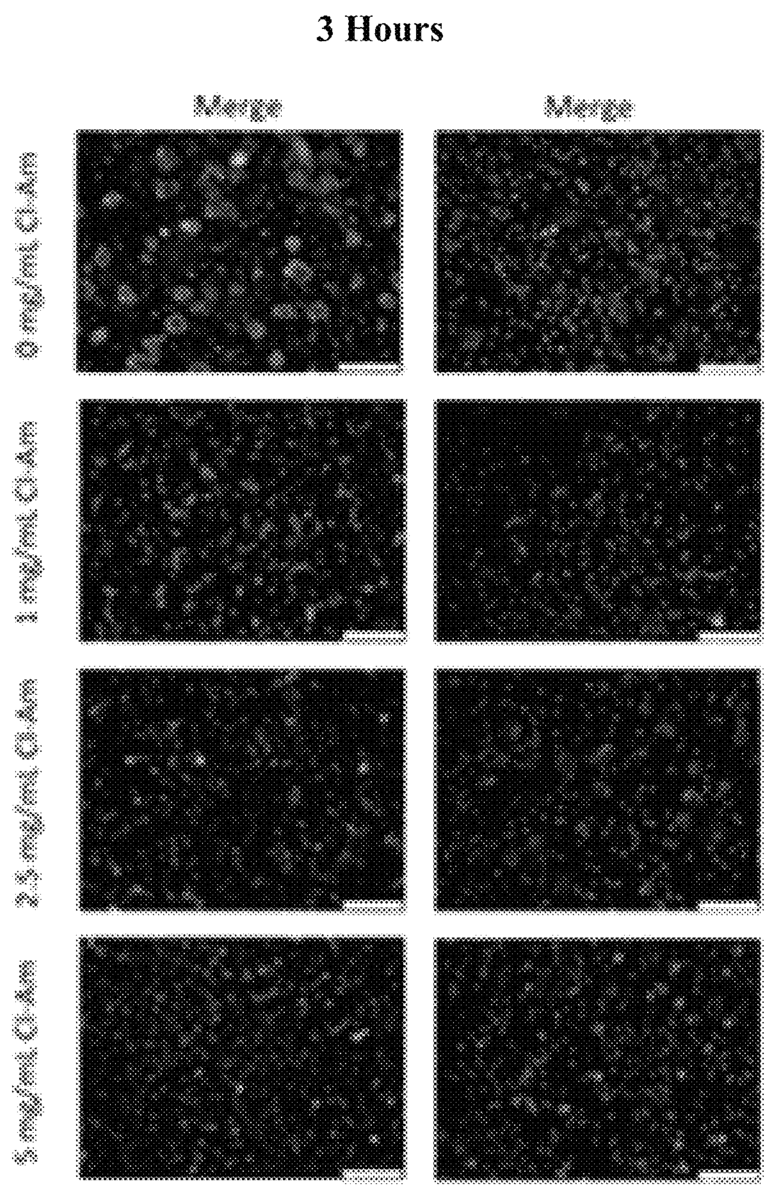
FIG. 11A is a series of images of merged DAPI and SYTOX Green staining comparison of small diameter (left column) and large diameter (right column) templates at 3 hours.
Figure 11B:
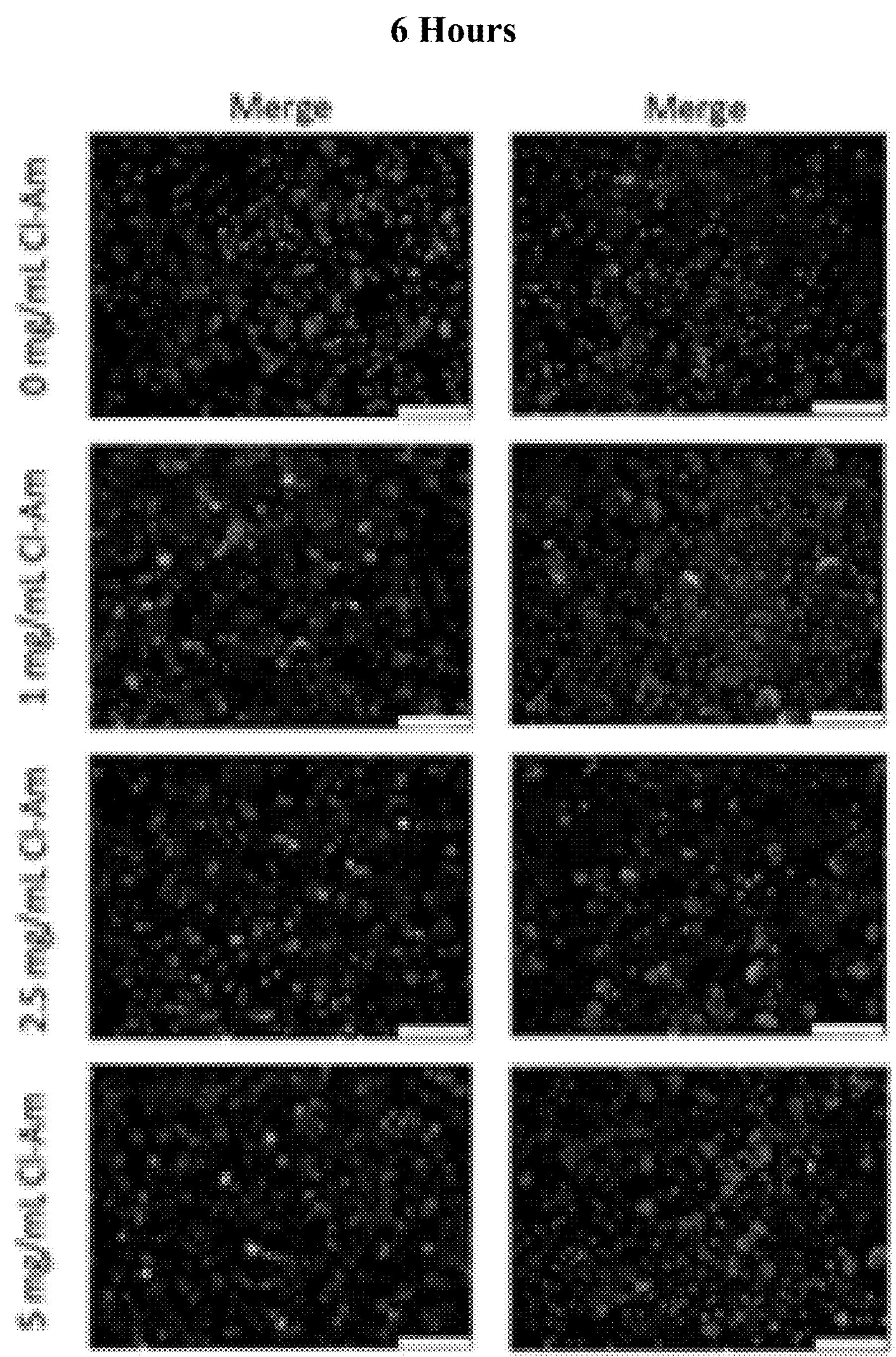
FIG. 11B is a series of images of merged DAPI and SYTOX Green staining comparison of small diameter (left column) and large diameter (right column) templates at 6 hours.

Small diameter and large diameter templates were fabricated with 0 to 5 mg/mL Cl-amidine with optimized parameters (FIGS. 7A to 7D). PDO (Sigma Aldrich Co.) was dissolved overnight in HFP at varying concentrations (Table 1) ranging from 65 to 100 and 170 to 200 mg/mL to create SD and LD templates, respectively. 0, 1, 2.5, or 5 mg/mL of Cl-amidine was added to the polymer solution and dissolved for 2 h with gentle agitation before electrospinning. Solutions were loaded into a syringe with an 18-gauge blunt needle tip attached to the positive lead of a power source (Spellman CZE1000R, Spellman High Voltage Electronics Corp.) and placed on a syringe pump (Model No. 78-01001, Fisher Scientific). Solutions were electrospun with optimized flow rate, airgap distance, and applied voltage (Table 1). Fibers were collected on a grounded, stainless steel rectangular mandrel (200×750×5 mm) that was rotating at 1,250 rpm and translating 6.5 cm/s over 13 cm. The templates (thickness 0.10-0.25 mm) were stored at −20.0 until analyses. Scanning electron micrographs (SEMs) were obtained for fiber (n=250) and pore (n=60) diameter analysis using Fibraquant 1.3 software. For scanning electron microscopy, templates were coated with 5 nm of gold-palladium by sputter coating in an argon gas field. The materials were then imaged with a FEI Nova NanoSEM 650 with field emission gun at +20 kV with a working distance of 5 mm to generate scanning electron micrographs (SEMs). Fiber diameter and pore diameter were characterized by analyzing the SEMs in FibraQuant 1.3 software (nanoTemplate Technologies, LLC). Average fiber and pore diameters with corresponding standard deviations were determined from a minimum of 250 semi-automated random measurements per image and 60 random manual measurements per image, respectively. FIGS. 7A and 7B provide micrographs showing small diameter and large diameter fibers, respectively. Small diameter templates (FIG. 7A) and large diameter templates (FIG. 7B) have uniform fiber and pore morphologies. Small diameter templates have significantly smaller fiber diameters (FIG. 7C) compared to large diameter templates ($p<0.05$). Small diameter templates have significantly smaller pore diameters (FIG. 7D) compared to large diameter templates ($p<0.05$). No differences in fiber or pore diameter were observed due to drug content. Small diameter Fibers: 0.36±0.16 μm large diameter Fibers: 1.82±0.59 μm.

TABLE 1

Electrospun templates were fabricated with optimized parameters.

| | Polymer concentration [mg/mL] | Cl-Am concentration [mg/mL] | Flow rate [mL/h] | Airgap distance [cm] | Applied voltage [+kV] |
|---|---|---|---|---|---|
| SD | 85 | 0 | 2 | 13 | 22 |
| | 100 | 1 | 2.5 | 15 | 18 |
| | 100 | 2.5 | 2.5 | 15 | 18 |
| | 100 | 5 | 2.5 | 15 | 18 |
| LD | 170 | 0 | 6 | 13 | 22 |
| | 200 | 1 | 3 | 18 | 28 |
| | 200 | 2.5 | 3 | 18 | 28 |
| | 200 | 5 | 3 | 18 | 28 |

Polymer and Cl-Am concentration were varied to create two distinct groups of SD and LD templates.

Cl-amidine elution from template was characterized as follows. 10 mm diameter discs of the templates (n=6) were placed in 48-well culture plate, and the templates were incubated with 300 μL of HBSS for 15 minutes to 5 days (media refreshed at each time point). Cl-amidine elution was determined with a PAD4 Inhibitor Screening Assay (FIGS. 8A to 8D).

FIG. 6 shows the four-parameter regression curve for the HFP samples along with the HBSS samples. As the concentration of drug increases, the relative fluorescence decreases, signifying an increase in the inhibition of PAD4. The assayed drug concentrations were selected to provide a range that includes the IC50 of Cl—Am against PAD4, which is 5.9 μM in an in vitro model (Luo et al., 2006). Exposure of Cl—Am to HFP significantly reduced its activity against PAD4 at two concentrations, 5.9 and 29.5 μM ($p<0.0001$). However, the drug was still active producing a sigmoidal curve similar to that of the HBSS samples. The drug retained efficacy after exposure to HFP and inhibited PAD4 activity at concentrations as low as 1.2 μM, demonstrating the potential to incorporate it into electrospun templates for release and activity against PAD4.

In addition to determining the activity of Cl—Am, the samples exposed to HFP were used to create a standard curve for quantifying unknown Cl—Am concentrations. The four-parameter logistic regression of the HFP exposed samples (Equation 1, x=logarithmic transform of Cl—Am concentration and y=relative fluorescence) has an R2-value of 0.996, and there is no evidence of an inadequate model from the lack of fit test (p=0.28).

$$y = \frac{2.65}{1 + 10^{5.25+1.14x}}, \quad \text{Equation 1(HFP)}$$

wherein "y" is relative fluorescence and X is log(M) and "M" is logarithmic transform of Cl-amidine concentration (i.e., the log transform of molarity). Lower fluorescence indicated greater inhibition of PAD4. No evidence of lack of fit (p=0.28) was found for the four-parameter regression of HFP exposed samples. Significant loss of activity was observed at two concentrations. This provided a standard curve for quantifying unknown Cl-amidine from elution studies.

Example 5: In Vitro Evaluation with Fresh Human Peripheral Blood Neutrophils

Figure 12A:
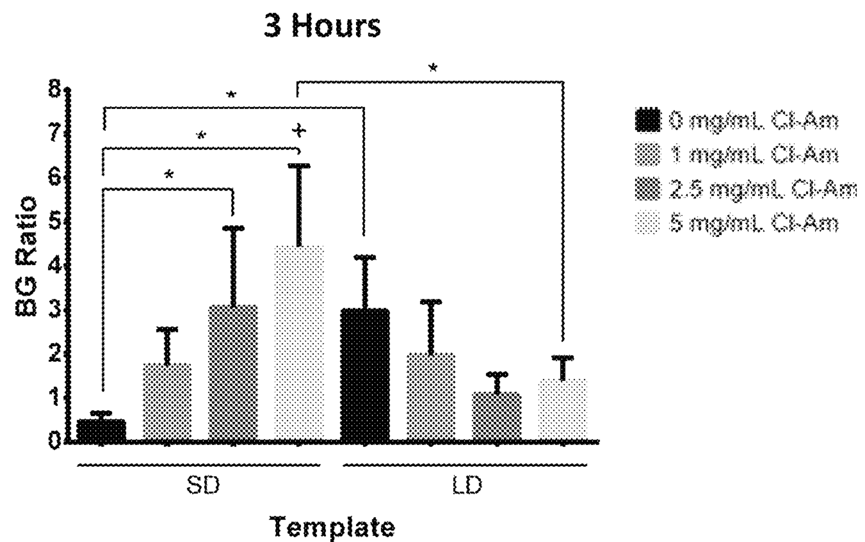
FIGS. 12A and 12B (A) graphically summarize the results observed in FIGS. 11A and 11B.
Figure 12B:
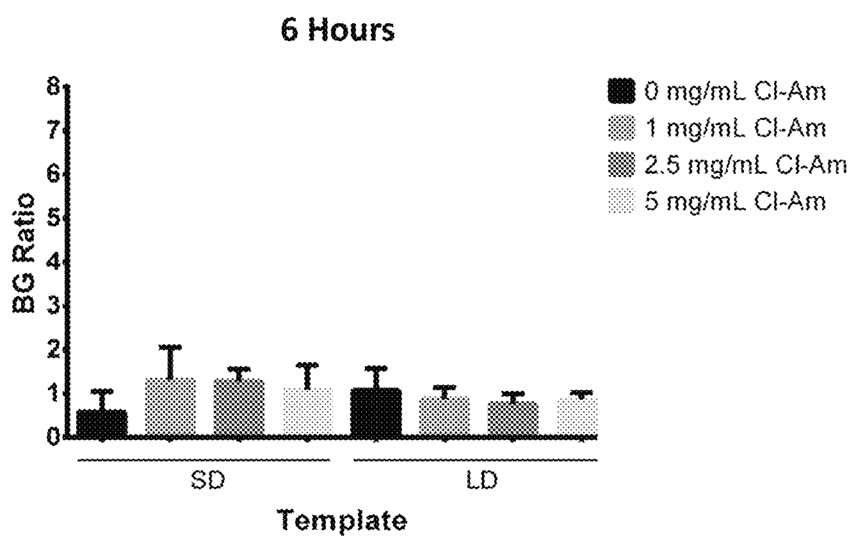

The effect of Cl-amidine impregnated template was evaluated as follows. 10 mm diameter punches of the templates (n=4) were placed in a 48-well culture plate and disinfected by UV irradiation. Isolated peripheral neutrophils from whole blood were suspended in sterile HBSS and used to seed templates with 600,000 cells in 250 μL of HBSS and cultured for 3 and 6 hours under standard conditions. Cellularized templates were then fixed in 10% buffered formalin and fluorescence quantification of NETs was carried out. Templates with 100 nM SYTOX Green for extracellular DNA followed by DAPI fixed cell nuclei stain at stock concentration (FIGS. 9A, 9B, 10A, 10B, and 11A). The ratio of DAPI (blue) to SYTOX green (BG ratio) pixels per image using MATLAB 2012a was quantified to determine degree of NETosis (FIGS. 12A and 12B).

Infrared scanning and quantification of citrullinated histone H3 (CitH3) was carried out as follows. Templates were incubated with rabbit anti-human histone H3 (citrulline R2+R8+R17) antibody (ABCAM) followed by IRDye 800CW donkey anti-rabbit secondary antibody. The templates were scanned on the 800-nm channel of the Odyssey CLx Infrared Imaging System (LICOR) to generate full-thickness template fluorescence. Template-bound CitH3 was quantified with standard curve of CitH3 vacuum blotted onto a PVDF membrane. Statistical analysis was carried out as follows. An unpaired T test was used to compare differences in activity of Cl-amidine. The plot of average fluorescent intensity against Cl-amidine concentration was fit with a four-parameter logistic regression and executed a lack of fit test. Then the plot of relative fluorescence against mass of CitH3 was fit with a linear regression. A two-way analysis of variance (ANOVA) and a Tukey multiple comparison procedure was used for all other in vitro analysis of data, which was performed in GraphPad Prism 6 at a significance level of 0.05.

FIGS. 8A to 8D quantitate Cl-amidine elution kinetics. Small diameter templates (FIGS. 8A and 8C) eluted significantly more drug than the large diameter templates (FIGS. 8B and 8D) over the 5 days. This is a function of the high surface area of small diameter fibers. In the first 3 hours, small diameter and large diameter templates eluted nearly 60% of the total drug released. There was a burst due to segregation of charged drug to outer surface of fibers, which makes it ideal for modulation of acute, local inflammation.

Figure 13A:
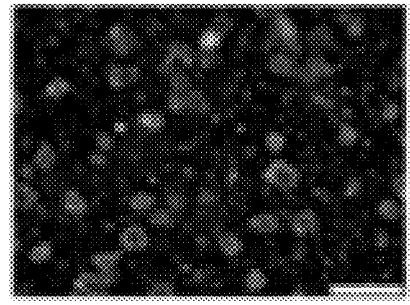
FIGS. 13A and 13B are micrographs.
Figure 13A:
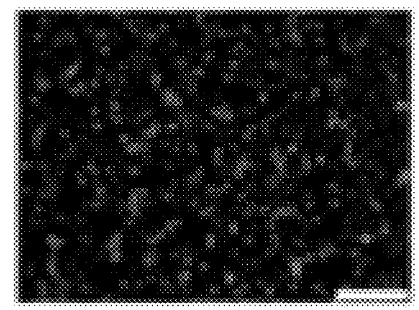
Figure 13A:
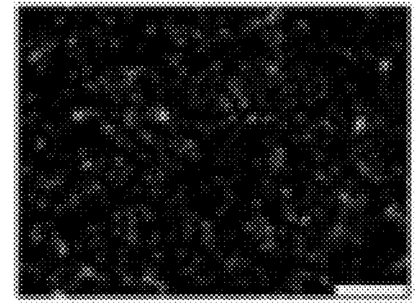
Figure 13A:
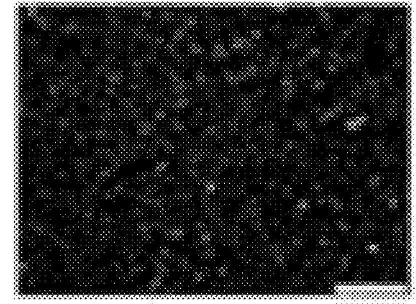
Figure 13B:
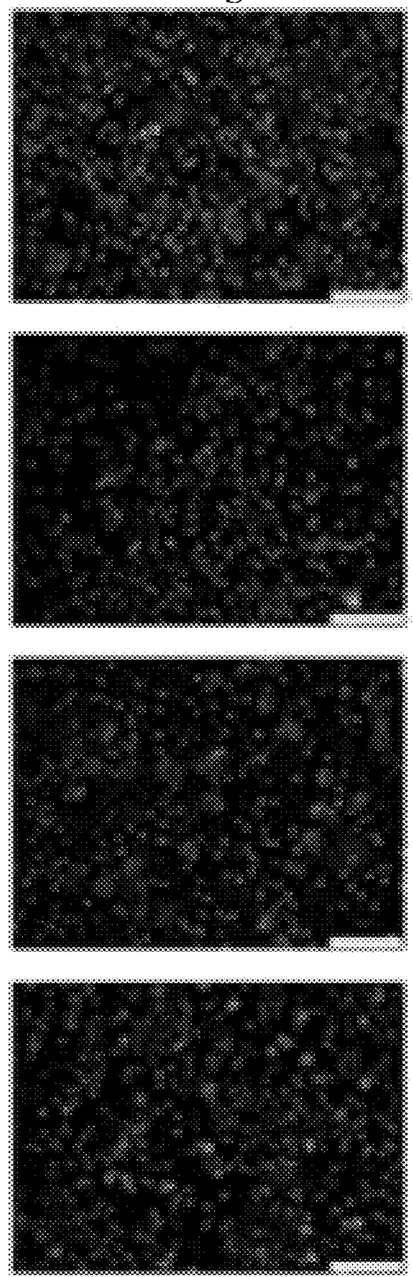
Figure 14A:
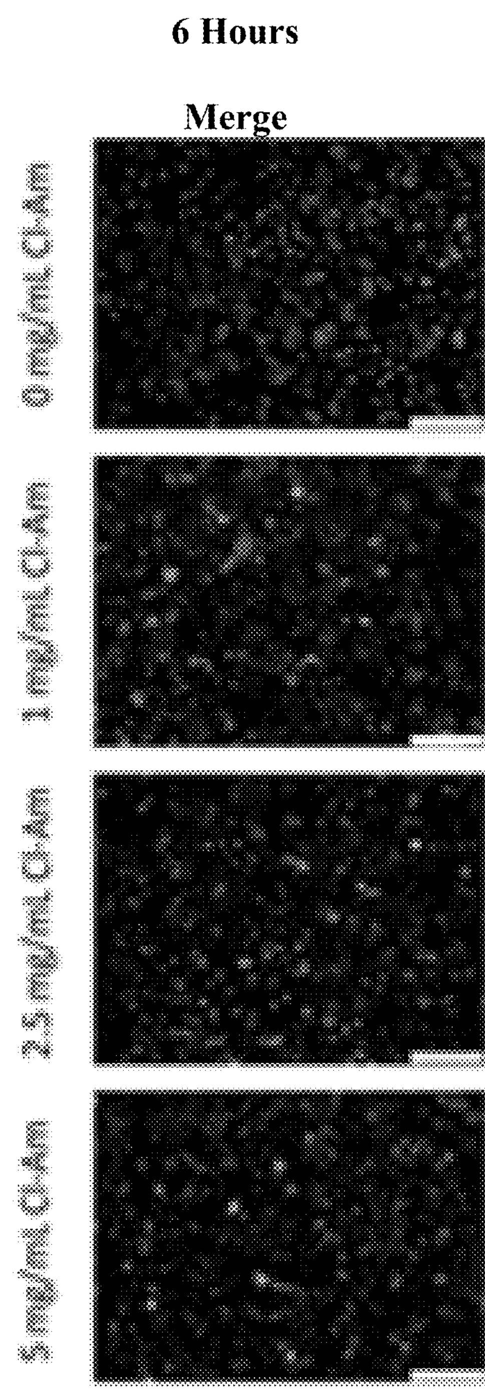
FIGS. 14A and 14B show the effects of Cl-amidine on Netosis.
Figure 14B:
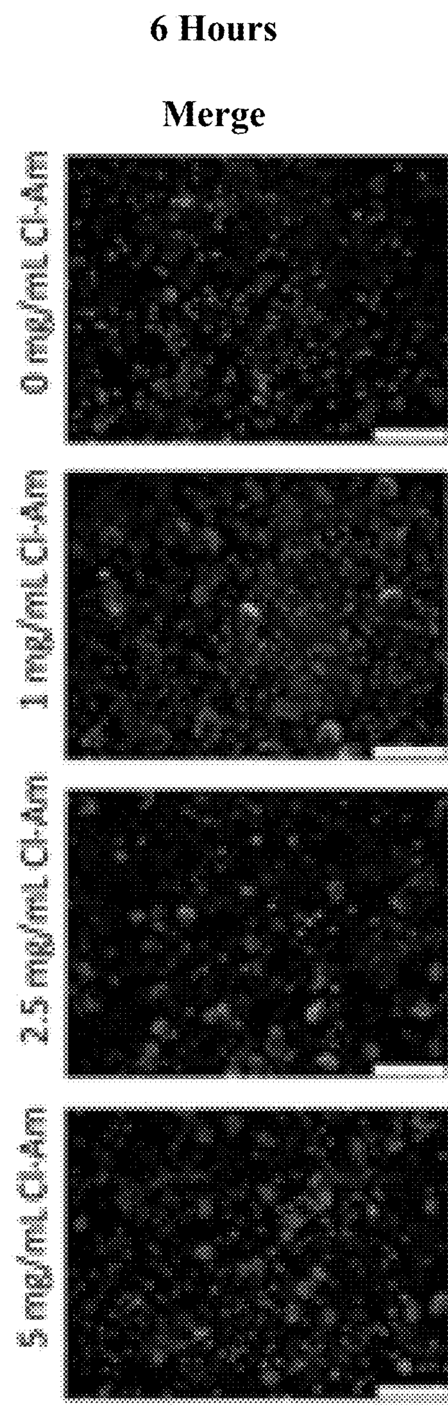

FIGS. 10A, 10B, 11A, and 11B show the effect of templates eluting Cl-amidine, which modulated NETosis in vitro. FIGS. 12A and 12B show that small diameter and large diameter templates have different effects on NETosis based on drug content. A BG ratio greater than 1 indicates more intact cells, while a BG ratio less than 1 indicates more extruded NETs. Significantly more NETs on small diameter templates at 3 hours (FIG. 12A) compared to large diameter templates (p<0.05). Cl-amidine significantly attenuated NETosis on small diameter templates at 3 hours (p<0.05) with an opposite trend on large diameter templates. Nearly equivalent NETs were observed at 6 hours (FIG. 12B). FIGS. 13A and 13B plot the differences observed.

Figure 17A:
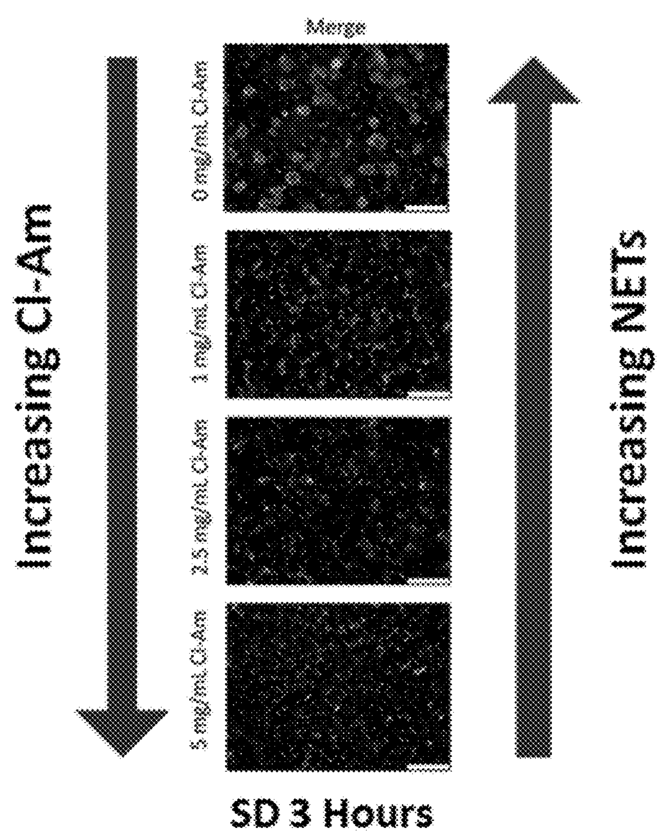
FIGS. 17A and 17B provide models for the effects of Cl-amidine on NETosis.
Figure 17B:
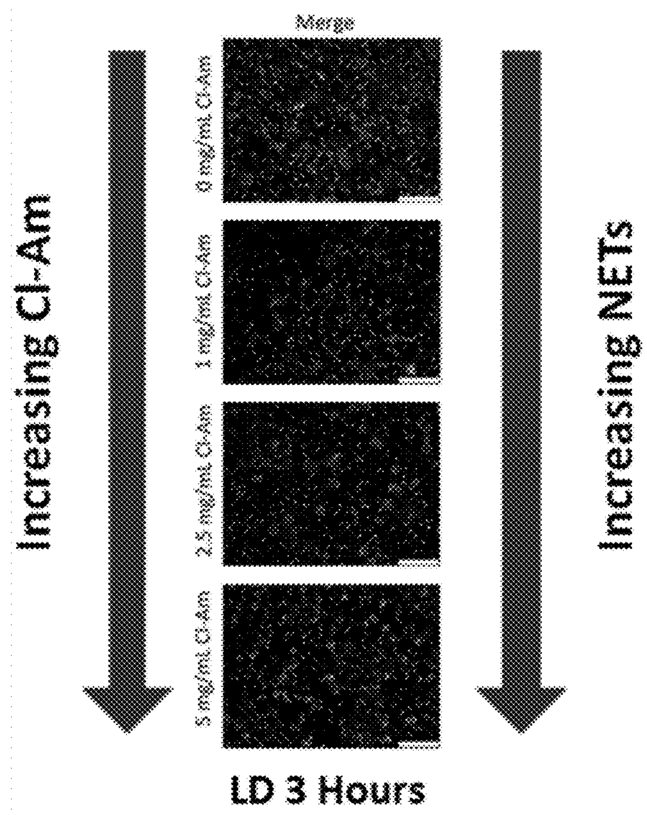

DNA-bound citrullinated histone H3 (contained within extruded NETs on the templates was evaluated. FIGS. 13A, 13B, 14A, and 14B show different degrees of NETosis. FIG. 15 depicts an equation where y is relative fluorescence and X is mass of CitH3 in ng (R2=0.966). The equation y=91.1x, where y is relative fluorescence and X is mass of CitH3 in ng (R2=0.966) was used to evaluate the reflected microscopy results for small diameter templates (FIG. 16A), but did not apply for large diameter templates (FIG. 16B). Without wishing to be bound by theory, these results may implicate alternative NETosis pathways (FIGS. 17A and 17B).

Figure 18:
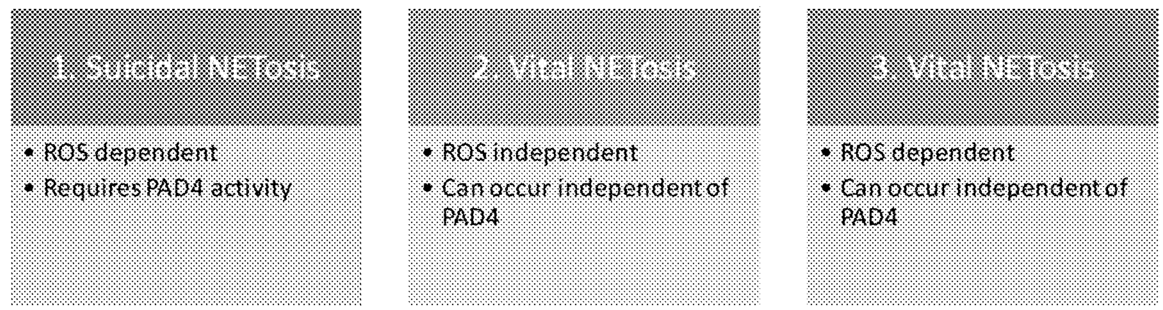
FIG. 18 is a schematic of NETosis pathways.

The invention provides dose-dependent modulation of NETosis on small diameter templates for local regulation. Large diameter template results may indicate template-induced NETosis independent of PAD4-mediated histone H3 deimination. Without wishing to be bound by theory, there may be three pathways of NETosis regulated by receptor signaling (FIG. 18).

In sum, electrospun PDO eluting Cl-amidine can be used to modulate NETosis, thereby regulating acute inflammation and the early innate immune response. This result was also demonstrated in vivo. These results demonstrated the significance of designing immunomodulatory biomaterials that regulate the neutrophil interaction and that have applications beyond biomaterial-guided tissue regeneration.

Example 6

The polarity of the applied voltage (i.e. positive or negative) during the electrospinning process can determine how a charged molecule or drug segregates within an electrospun fiber, thus altering the elution profile. To determine the elution profile of amidine, a charged drug, its elution from polydioxanone (PDO) electrospun fibers was quantified.

PDO (Bezwada Biomedical LLC) was dissolved overnight in 1,1,1,3,3,3-hexafluoro-2-propanol (HFP, Oakwood Products, Inc.) at varying concentrations (Table 2) ranging from 72 to 90, 85 to 140, and 135 to 200 mg/mL to create small diameter, intermediate diameter (INT), and large diameter templates, respectively. 0, 1, 2.5, or 5 mg/mL of Cl-amidine was added to the polymer solution and dissolved for 2 hours with gentle agitation before electrospinning. Solutions were loaded into a syringe with an 18-gauge blunt needle tip attached to the lead of a power source (Spellman CZE1000R, Spellman High Voltage Electronics Corp.) and placed on a syringe pump (Model No. 78-01001, Fisher Scientific). Solutions were electrospun with optimized flow rate, airgap distance, and applied voltage (Table 1). Fibers were collected on a grounded, stainless steel rectangular mandrel (200×750×5 mm) that was rotating at 1,250 rpm and translating 6.5 cm/s over 13 cm.

TABLE 2

Electrospun templates were fabricated with optimized parameters.

| Sample ID | Polymer Concentration [mg/mL] | Cl-Amidine Concentration [mg/mL] | Flow Rate [mL/h] | Air Gap Distance [cm] | Polarity | Applied Voltage [kV] |
|---|---|---|---|---|---|---|
| SD + 0 POS | 72 | 0 | 0.6 | 13 | + | 13 |
| SD + 0 NEG | 72 | 0 | 0.6 | 13 | − | 13 |
| SD + 1 POS | 90 | 1 | 0.9 | 16 | + | 16 |
| SD + 1 NEG | 80 | 1 | 0.5 | 8 | − | 8 |
| SD + 2.5 POS | 85 | 2.5 | 1.1 | 12 | + | 12 |
| SD + 2.5 NEG | 85 | 2.5 | 0.9 | 12 | − | 12 |
| SD + 5 POS | 95 | 5 | 2.5 | 18 | + | 18 |
| SD + 5 NEG | 90 | 5 | 2.5 | 18 | − | 18 |
| INT + 0 POS | 85 | 0 | 2.3 | 24 | + | 24 |
| INT + 0 NEG | 85 | 0 | 2.3 | 24 | − | 24 |
| INT + 1 POS | 125 | 1 | 3.5 | 22 | + | 22 |
| INT + 1 NEG | 125 | 1 | 3.5 | 22 | − | 22 |
| INT + 2.5 POS | 110 | 2.5 | 4 | 20 | + | 20 |
| INT + 2.5 NEG | 110 | 2.5 | 4 | 20 | − | 20 |
| INT + 5 POS | 140 | 5 | 3.5 | 22 | + | 22 |
| INT + 5 NEG | 140 | 5 | 3.5 | 22 | − | 22 |
| LD + 0 POS | 135 | 0 | 4 | 25 | + | 25 |
| LD + 0 NEG | 135 | 0 | 4 | 25 | − | 25 |
| LD + 1 POS | 180 | 1 | 3.5 | 18 | + | 18 |
| LD + 1 NEG | 190 | 1 | 3.5 | 18 | − | 18 |
| LD + 2.5 POS | 200 | 2.5 | 3.5 | 22 | + | 22 |
| LD + 2.5 NEG | 200 | 2.5 | 3 | 20 | − | 20 |
| LD + 5 POS | 200 | 5 | 3.5 | 22 | + | 22 |
| LD + 5 NEG | 200 | 5 | 3.5 | 18 | − | 18 |

To characterize the templates, scanning electron microscopy was performed. Templates were coated with 5 nm of gold-palladium by sputter coating in an argon gas field. The materials were then imaged with a FEI Nova NanoSEM 650 with field emission gun at +20 kV with a working distance of 5 mm to generate scanning electron micrographs (SEMs). Fiber diameter and pore diameter were characterized by analyzing the SEMs in FibraQuant 1.3 software (nanoTemplate Technologies, LLC). Average fiber diameters with corresponding standard deviations were determined from a minimum of 150 semi-automated random measurements per image and 60 random manual measurements per image, respectively.

Electrospun templates were characterized for the delivery of Cl-amidine into supernatant over 5 days. 10 mm diameter discs of the templates (n=3) were placed in a 48-well culture plate, and 300 μL of HBSS were added to each well. After incubation at 37° C. for 15, 30, and 45 minutes; 1, 2, 3, and 6 hours; and 1, 2, 3, 4, and 5 days, the supernatant was removed and refreshed with 300 μL of HBSS. The collected supernatant was frozen and stored at −20° C. until analysis. Activity of Cl-amidine was detected using the PAD4 Inhibitor Screening Assay following manufacturer protocol, and the resulting fluorescent intensities were used to determine Cl-amidine concentration within the samples. An average and standard deviation were determined for each template type.

Analysis of data was conducted using a two-way analysis of variance (ANOVA) and a Tukey multiple comparison procedure. All statistical analyses were performed in GraphPad Prism 6 at a significance level of 0.05.

Figure 19A:
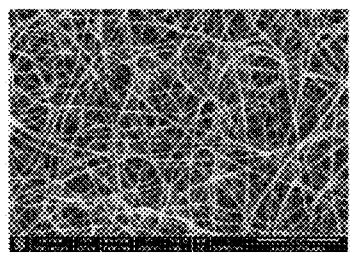
FIGS. 19A to 19C are representative scanning electron micrographs (SEMs) of the electrospun templates
Figure 19B:
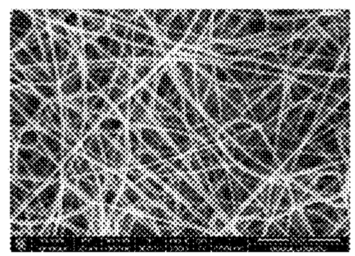
Figure 19C:
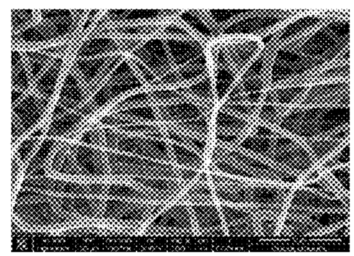
Figure 20C:
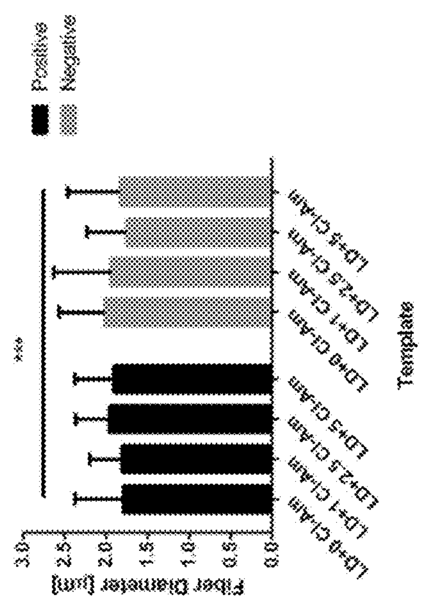
FIGS. 20A to 20C show the fiber diameters of electrospun fibers with 0-5 mg/mL Cl-amidine (Cl—Am).
Figure 20B:
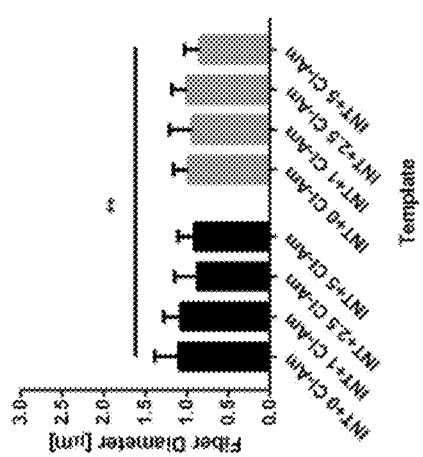
Figure 20A:
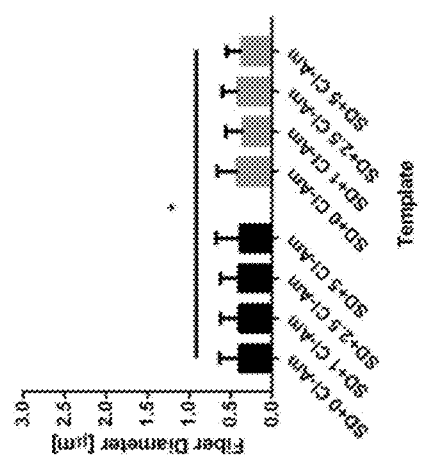
Figures 21E, 21F:
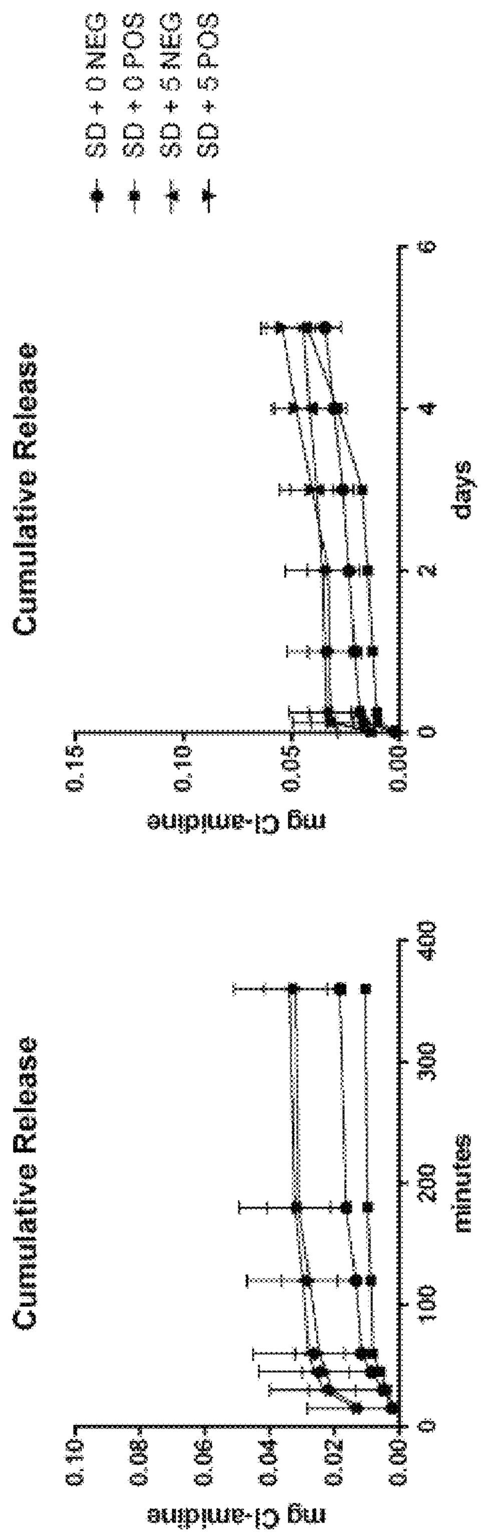
Figures 22E, 22F:
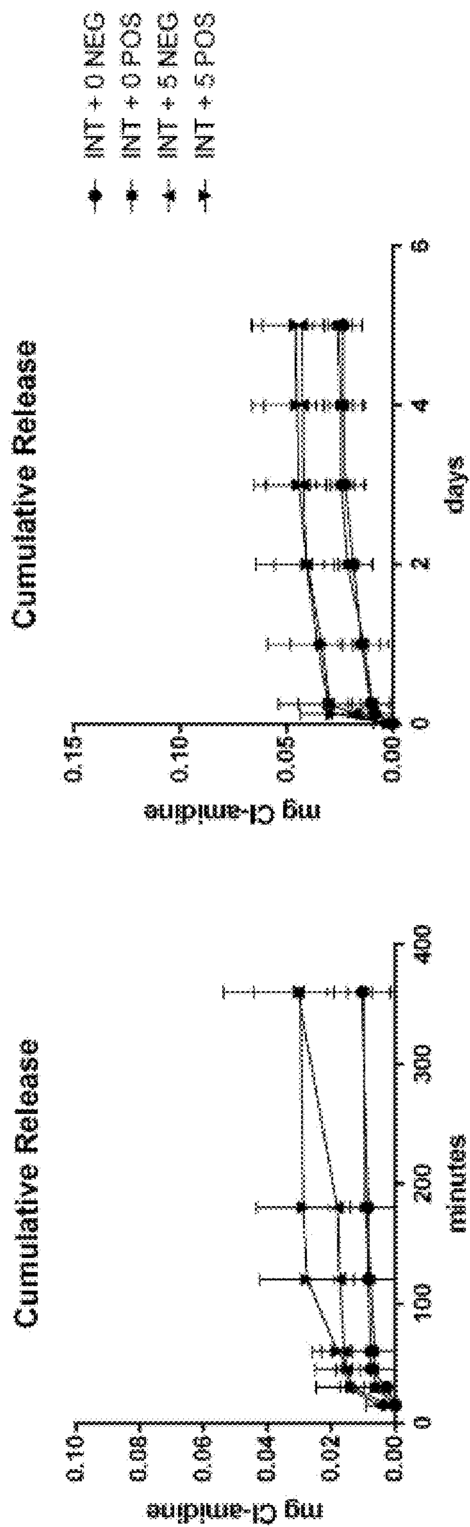
Figure 23F:
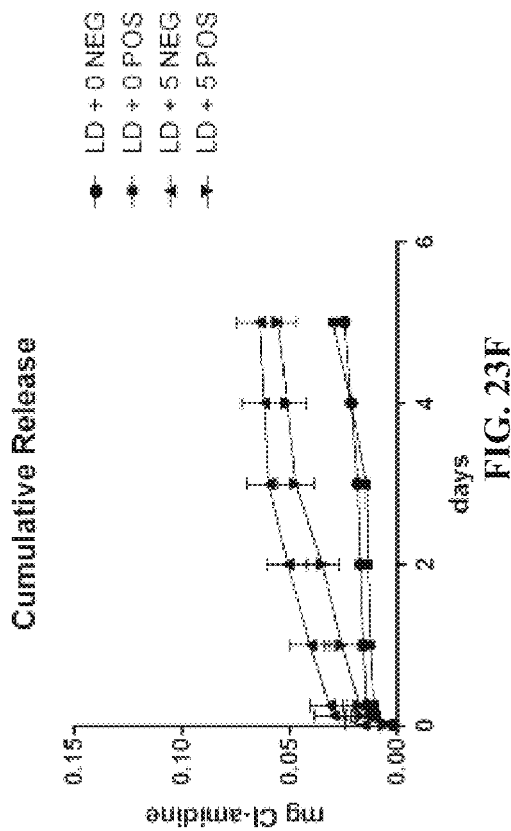
Figure 23E:
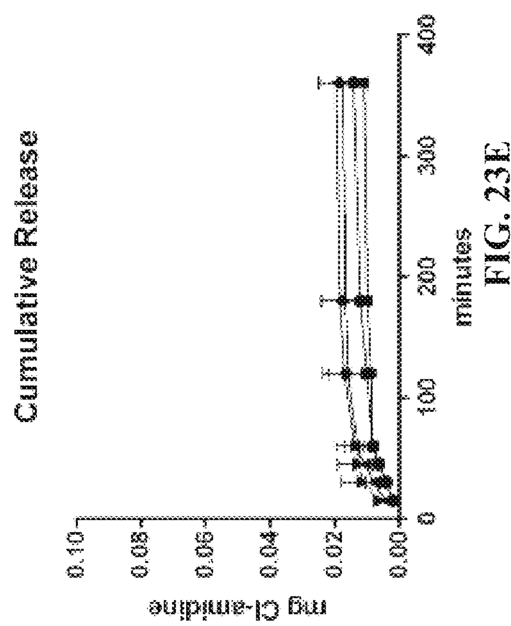

Low, intermediate, and high polymer concentration solutions incorporating Cl-amidine resulted in three distinct templates groups, small diameter, intermediate diameter, and large diameter templates, which had uniform fiber morphologies (FIGS. 19A to 19C). The addition of a charged entity (i.e., Cl-amidine) to the polymer solution can alter fiber diameter, so polymer concentration was adjusted to maintain consistent fiber diameters for all drug concentrations. Referring to FIGS. 20A to 20C, the small diameter, intermediate diameter, and large diameter template groups did not have significantly different fiber diameters between 0 and 5 mg/mL Cl-amidine. Additionally, there were no statistical differences observed between template counterparts fabricated with positive and negative applied voltages. At each drug concentration, the small diameter templates had significantly smaller fiber diameters with an average of 0.39±0.22 μm compared to the intermediate diameter and large diameter templates with average fiber diameters of 0.96±0.23 μm and 1.87±0.48 μm, respectively ($p<0.05$). Together, these data show that adjusting polymer concentrations compensated for the addition of Cl-amidine to produce templates with consistent fiber diameters, allowing elucidation of the effects of electrospinning polarity on drug elution.

Interestingly, the electrospinning polarity did not significantly affect the elution profiles of Cl-amidine from the electrospun templates over 5 days (FIGS. 21A to 21F, 22A to 22F, and 23A to 23F). The positive and negative polarities generated near identical elution profiles for 1, 2.5, and 5 mg/mL Cl-amidine for small diameter, intermediate diameter, and large diameter templates. In addition, all three fiber diameter templates fabricated with positive and negative applied voltages eluted approximately 60% of Cl-amidine released over the 5-day period within the first 3 hours. This burst release is ideal for targeting the innate immune response and acute inflammation within the first several hours after biomaterial implantation. These data show that the electrospinning polarity cannot be used to further tailor the Cl-amidine elution profile from electrospun templates to inhibit inflammation. Nonetheless, fiber size, fiber composition, and drug concentration offer three other independent mechanisms that can be utilized to create unique materials for specific applications regarding inflammation inhibition.

Example 7: In Vivo Rat Subcutaneous Implant Model

Ten millimeter diameter discs of the templates (n=3) were implanted on the back of Sprague-Dawley rats (300-325 g, male) following the protocol approved by the University of Memphis Institutional Animal Care and Use Committee as previously described (Fetz et al., 2017). Briefly, templates were disinfected with UV irradiation for 10 min on each side, and all materials were handled aseptically. One template lying flat was implanted per subcutaneous pocket, and the skin was closed with 2-3 staples. Four templates were implanted randomly on the back of each rat. Additionally, to ensure drug eluting materials exerted their effects locally without diffusion or convection to adjacent samples, two small diameter templates with 0 mg/mL Cl—Amidine were implanted between four small diameter templates with 5 mg/mL Cl-amidine (n=3), and two small diameter templates with 0 mg/mL Cl-amidine (n=3) were implanted alone. One day after implantation, the animals were euthanized, the subcutaneous pockets were opened, and the templates were explanted, fixed, and stored in 10% neutral buffered formalin at 4° C. Fixed templates were processed, sectioned at 10 μm, and stained with hematoxylin and eosin (H&E) following standard protocol. The sections were evaluated and scored by a board certified veterinary pathologist blinded to sample identity for presence of surface DNA, invasion into the template, and degree of neutrophil degeneration (Table 3). The presence of surface DNA was evaluated based on prevalence of DNA on the surfaces of the templates seen as a blue-stained acellular layer, invasion into the templates was scored based on number of invading neutrophils and depth of invasion, and the degree of neutrophil degeneration was assessed based on the abundance of neutrophils showing degenerative morphological changes (i.e., loss of lobulated nuclei, fragmentation, apoptotic bodies, etc.). Finally, the surface of the 1-day templates were evaluated for template-bound CitH3 through an On-cell Western blot following the in vitro protocol.

TABLE 3

Electrospun templates were evaluated by a veterinary pathologist in a blinded fashion at 1 day after implantation in a subcutaneous rat implant model.

| Score | Presence of surface DNA | Invasion into the template | Degree of neutrophil degeneration |
|---|---|---|---|
| 1 | DNA adherent to some surfaces of the template | Slight invasion into the template near a fold or defect in the template | Most invading neutrophils non-degenerative |
| 2 | DNA adherent to most surfaces of the template | Slight invasion into the template | Many invading neutrophils non-degenerative |
| 3 | Dense DNA layer adherent to some surfaces of the template | Moderate invasion with reduced invasion towards the center of the template | Occasional invading neutrophils non-degenerative |
| 4 | Dense DNA layer adherent to most surfaces of the template | Moderate invasion throughout the thickness of the membrane | Few non-degenerating neutrophils not deeply invaded |
| 5 | Conspicuous, dense DNA layer adherent to the surfaces of the template | Dense invasion throughout the thickness of the membrane | Diffuse degenerating neutrophils near the surface of defect in the template. |

Figure 24A:
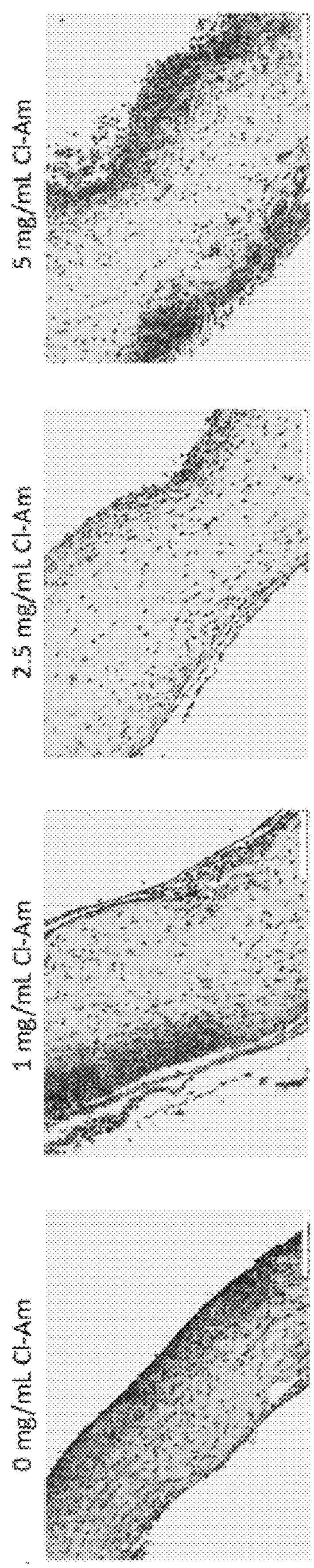
FIGS. 24A and 24B show Cl-amidine elution in vivo.
Figure 24B:
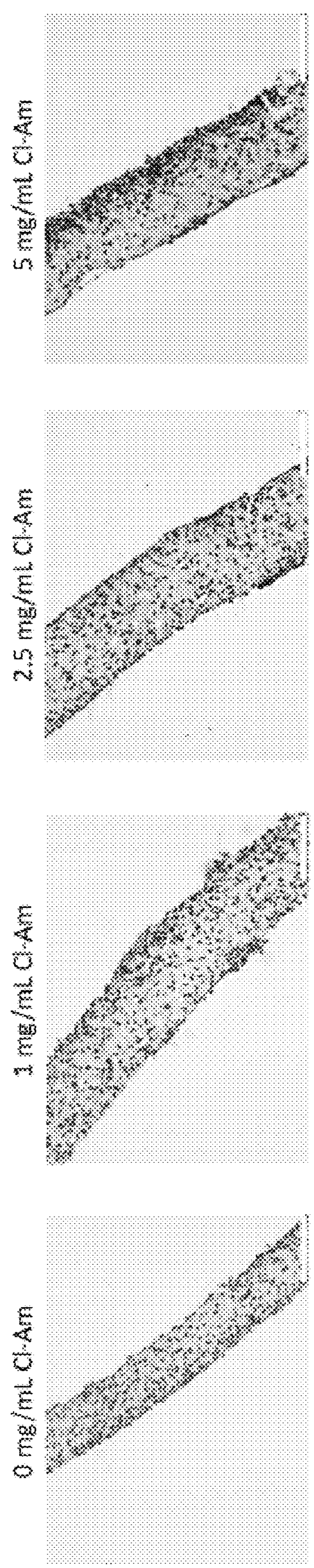
Figure 25A:
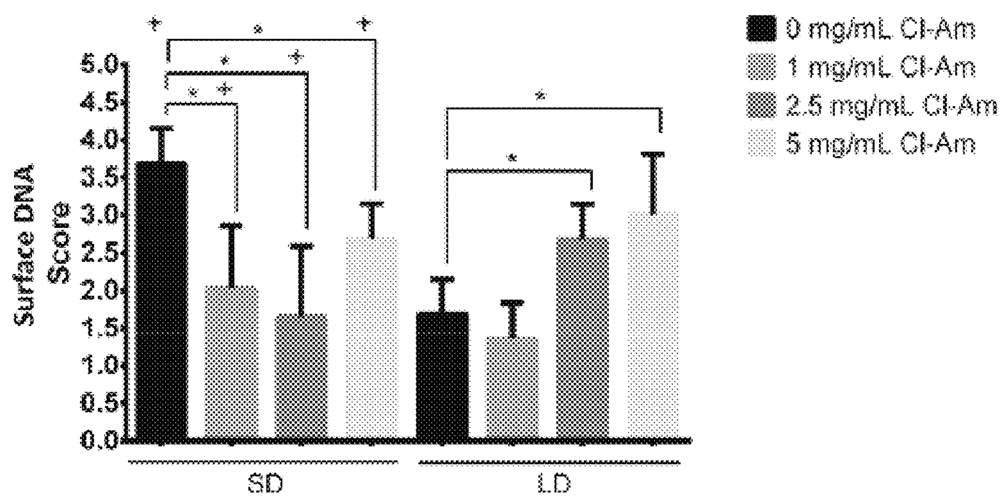
FIGS. 25A to 25C quantitate Cl-amidine elution impact on cell behavior in vivo.
Figure 25B:
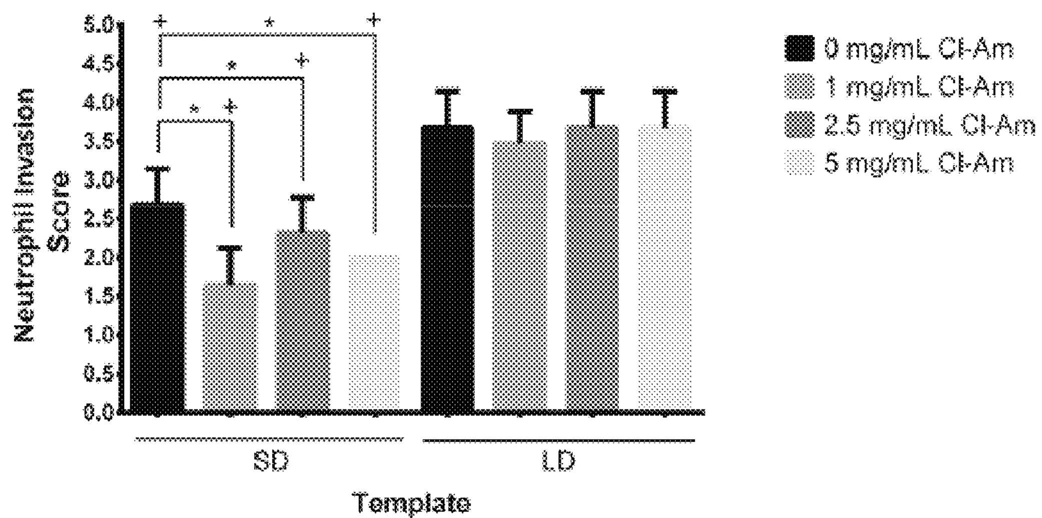
Figure 25C:
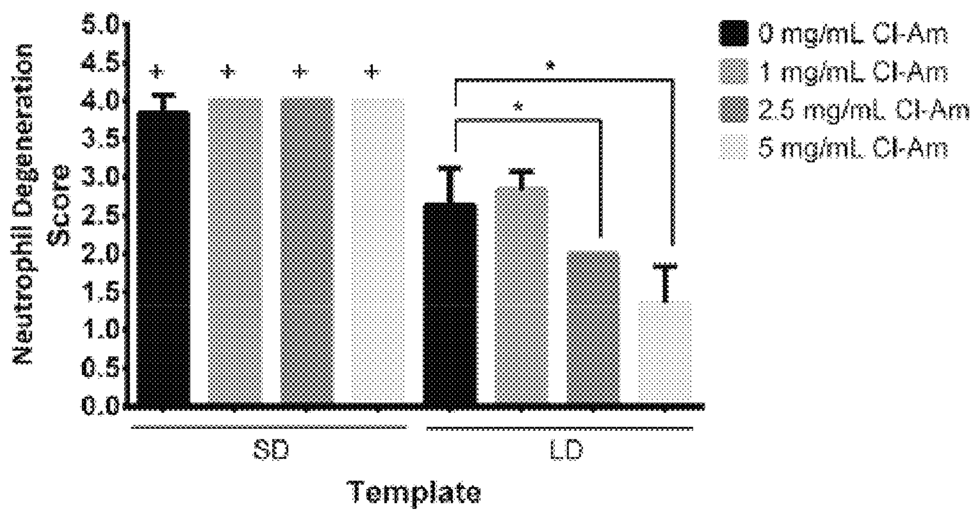
Figure 26:
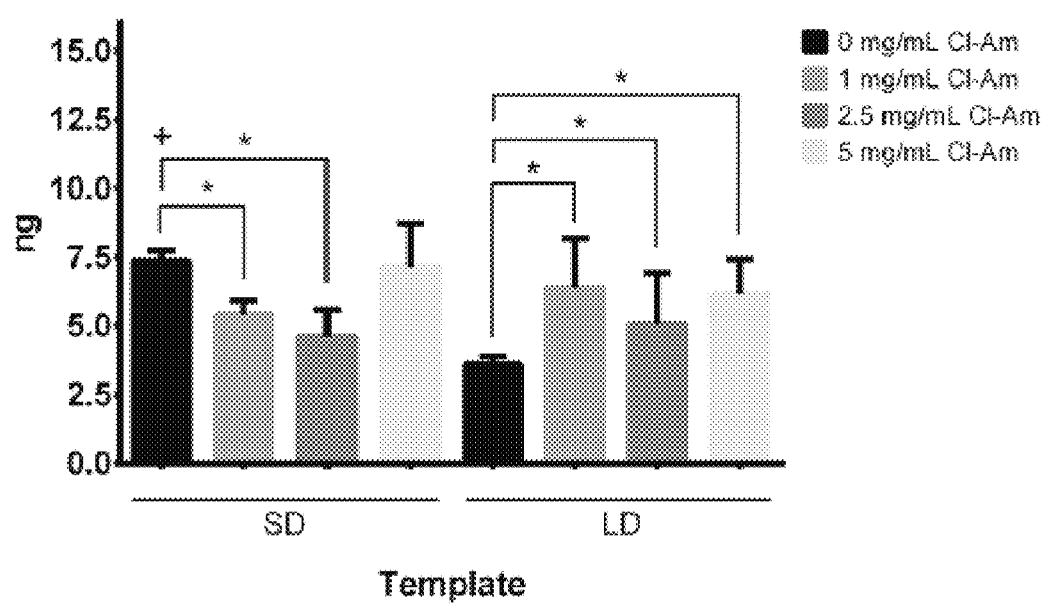
FIG. 26 is a graph illustrating PDO templates that elute Cl—Am modulate NETosis in vivo. Cl—Am attenuates NETosis as indicated by CitH3 on SD templates while increasing NETosis on LD templates. *Significant difference ($p<0.05$). +Significant difference between SD and LD templates ($p<0.05$) (mean±std. dev., n=3).

The Cl-amidine eluting electrospun templates were implanted subcutaneously on the back of rats. H&E staining of templates after 1 day (FIGS. 24A and 24B) indicated that small diameter and large diameter templates initiated differing responses based on template architecture and drug content, which were quantified by a veterinary pathologist in a blinded fashion. At 1 day, the presence of surface DNA, invasion into the template, and degree of neutrophil degeneration were evaluated (FIGS. 25A to 25C). The presence of surface DNA (FIG. 25A) scored significantly higher on small diameter templates with 0 mg/mL Cl-amidine at 3.7±0.5 compared to large diameter templates with 0 mg/mL Cl-amidine at 1.7±0.5 ($p<0.05$). A dense DNA layer was adherent to most surfaces on the small diameter the templates whereas only some DNA was adherent to the large diameter template surfaces, similar to the trends seen in vitro. For the small diameter templates, Cl-amidine significantly decreased the scores for the presence of surface DNA, while for large diameter templates, the opposite was observed ($p<0.05$). Again, these data reflect the fluorescence microscopy results in vitro, suggesting that Cl-amidine elution results in similar effects in a physiological environment. Interestingly, for the small diameter templates with 5 mg/mL Cl-amidine, the score for surface DNA was greater than the score for 1 and 2.5 mg/mL Cl-amidine; however, the score was still significantly lower compared to small diameter templates with 0 mg/mL Cl-amidine. Invasion of neutrophils into the templates (FIG. 25B) was also modulated by architecture and drug concentration. large diameter templates scored significantly higher with moderate invasion throughout the thickness of the template compared to small diameter templates with slight invasion into the template ($p<0.05$). Because of the restrictive pore diameters of the small diameter templates, which are 3 times smaller than the small diameter template pore diameters, it is not surprising that the small diameter templates exhibited less invasion. Interestingly, the elution of Cl—Am from small diameter templates significantly decreased invasion into the templates compared to the small diameter template with 0 mg/mL Cl—Am ($p<0.05$). This is not observed for the small diameter templates, which all scored with moderate invasion. The degree of neutrophil degeneration (FIG. 25C) was significantly different in response to the templates after acute interaction in vivo. As noted, the degeneration of neutrophils was classified by the degree of morphological changes. All of the small diameter templates scored significantly higher at 4.0±0.2 compared to small diameter templates at or below 2.6±0.5 ($p<0.05$). This equates to minimal non-degenerating neutrophils that are not deeply invaded and many invading, non-degenerative neutrophils, respectively. Importantly, with increasing Cl—Am concentration, the small diameter templates scored significantly better for neutrophil degeneration, decreasing from 2.6±0.5 for 0 mg/mL Cl—Am to 1.3±0.5 for 5 mg/mL Cl—Am ($p<0.05$). The decreasing scores suggest that with increasing Cl—Am concentration, a greater portion of the interacting neutrophils are viable and exerting their potential long-term effector functions to modulate the early-stage innate immune response. In addition to pathological evaluation, the templates excised after 1 day were evaluated for template-bound CitH3 (FIG. 26). The results show that the small diameter templates with 0 mg/mL Cl—Am had significantly more template-bound CitH3 with 7.3±0.4 ng compared to the small diameter templates with 0 mg/mL Cl—Am at 3.6±0.3 ng ($p<0.05$). With increasing drug concentration, the amount of template-bound CitH3 significantly decreased on the small diameter templates, while the opposite was observed on small diameter templates ($p<0.05$). However, the small diameter templates with 5 mg/mL Cl—Am resulted in more CitH3 compared to 1 and 2.5 mg/mL Cl—Am. These significant trends validate the scores categorized by the pathologist for presence of surface DNA on the templates, indicating that the Cl—Am eluting templates modulate NETosis in vivo. To ensure the Cl—Am eluting templates exhibited only local inhibition of PAD4, small diameter templates with 0 mg/mL Cl—Am were implanted between templates with 5 mg/mL Cl—Am. Small diameter templates with 0 and 5 mg/mL Cl—Am were selected to maximally challenge the effects of Cl—Am through its high and rapid release from the small diameter templates. The small diameter templates with 0 mg/mL Cl—Am adjacent to templates with 5 mg/mL Cl—Am were compared to small diameter templates with 0 mg/mL Cl—Am that were implanted alone. After 1 day, histological scores were not significantly different for presence of surface DNA, invasion into the template, and degree of neutrophil degeneration for the small diameter adjacent templates and the small diameter template controls ($p<0.05$). The presence of DNA scored 2.0±0.8 and 2.3±0.8, the invasion into the templates scored 3.0±0.7 and 3.0±0.9, and the degree of neutrophil degeneration scored 4.2±0.4 and 4.2±0.2 for the small diameter adjacent templates and the small diameter template controls, respectively. Together, these data verify that the Cl—Am eluting templates only exert local effects in the first 24 h in vivo and do not affect the response to adjacent materials through diffusion or local convection.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. An electrospun polydioxanone (PDO) template comprising an amount of N-α-benzoyl-N5-(2-chloro-1-iminoethyl)-L-ornithine amide (Cl-amidine), wherein the Cl-amidine has been added to a solution comprising polydioxanone (PDO) and 1,1,1,3,3,3-hexafluoro-2-propanol (HFP) and dissolved before electrospinning.

2. The template of claim 1, wherein the amount of Cl-amidine is sufficient to inhibit fibrosis.

3. The template of claim 1, wherein the amount of Cl-amidine is sufficient to inhibit inflammation.

4. The template of claim 1, wherein the amount of Cl-amidine is sufficient to inhibit a Peptidyl arginine deiminase.

5. The template of claim 1, wherein the amount of Cl-amidine is sufficient to inhibit PAD4.

6. A biomaterial vehicle comprising an electrospun polydioxanone (PDO) template and N-α-benzoyl-N5-(2-chloro-1-iminoethyl)-L-ornithine amide (Cl-amidine), wherein the Cl-amidine has been added to a solution comprising polydioxanone (PDO) and 1,1,1,3,3,3-hexafluoro-2-propanol (HFP) and dissolved before electrospinning.

7. A method for inhibiting fibrosis surrounding a template, the method comprising implanting in a body an electrospun polydioxanone (PDO) template comprising an amount of Cl-amidine sufficient to inhibit fibrosis, thereby inhibiting fibrosis, wherein the Cl-amidine has been added to a solution comprising polydioxanone (PDO) and 1,1,1,3,3,3-hexafluoro-2-propanol (HFP) and dissolved before electrospinning.

8. A method for inhibiting biomaterial surface conditioning NETosis, the method comprising implanting in a body a biomaterial comprising an electrospun polydioxanone (PDO) template and an amount of Cl-amidine sufficient to inhibit biomaterial surface conditioning NETosis, thereby inhibiting biomaterial surface NETosis, wherein the Cl-amidine has been added to a solution comprising polydioxanone (PDO) and 1,1,1,3,3,3-hexafluoro-2-propanol (HFP) and dissolved before electrospinning.

9. A method for inhibiting local NETosis surrounding a template, the method comprising implanting in a body an electrospun polydioxanone (PDO) template comprising Cl-amidine, thereby inhibiting NETosis, wherein the Cl-amidine has been added to a solution comprising polydioxanone (PDO) and 1,1,1,3,3,3-hexafluoro-2-propanol (HFP) and dissolved before electrospinning.

10. A method for regulating the response of cells that are resident in or that arrive at the site of scaffold insertion, the method comprising contacting the cells with an electrospun polydioxanone (PDO) template comprising Cl-amidine, wherein the Cl-amidine has been added to a solution comprising polydioxanone (PDO) and 1,1,1,3,3,3-hexafluoro-2-propanol (HFP) and dissolved before electrospinning.

11. A kit comprising an electrospun polydioxanone (PDO) template that comprises an amount of N-α-benzoyl-N5-(2-chloro-1-iminoethyl)-L-ornithine amide (Cl-amidine), wherein the Cl-amidine has been added to a solution comprising polydioxanone (PDO) and 1,1,1,3,3,3-hexafluoro-2-propanol (HFP) and dissolved before electrospinning.

12. The kit of claim 11, wherein the template is resorbable.

* * * * *